United States Patent
Khalifah et al.

(10) Patent No.: US 9,428,533 B2
(45) Date of Patent: Aug. 30, 2016

(54) INHIBITORS OF ADVANCED GLYCATION END PRODUCTS

(71) Applicant: NephroGenex, Inc., Princeton, NJ (US)

(72) Inventors: Raja G. Khalifah, Cary, NC (US); Roger E. Marti, Winterhur (CH)

(73) Assignee: Nephrogenex, Inc, Research Triangle Park, NC (US)

( * ) Notice: Subject to any disclaimer, the term of this patent is extended or adjusted under 35 U.S.C. 154(b) by 0 days.

(21) Appl. No.: 14/184,888

(22) Filed: Feb. 20, 2014

(65) Prior Publication Data
US 2014/0187506 A1    Jul. 3, 2014

Related U.S. Application Data

(63) Continuation of application No. 13/767,371, filed on Feb. 14, 2013, now abandoned, which is a continuation of application No. 12/964,322, filed on Dec. 9, 2010, now abandoned, which is a continuation of application No. 11/825,045, filed on Jul. 3, 2007, now abandoned.

(60) Provisional application No. 60/819,437, filed on Jul. 7, 2006.

(51) Int. Cl.
| | |
|---|---|
| *C07H 17/02* | (2006.01) |
| *C07D 401/04* | (2006.01) |
| *C07D 401/14* | (2006.01) |
| *C07D 405/14* | (2006.01) |

(52) U.S. Cl.
CPC .............. *C07H 17/02* (2013.01); *C07D 401/04* (2013.01); *C07D 401/14* (2013.01); *C07D 405/14* (2013.01)

(58) Field of Classification Search
CPC ............................ C07H 17/02; C07D 401/04
USPC ........ 514/27, 253.09, 43; 544/364; 536/28.8
See application file for complete search history.

(56) References Cited

U.S. PATENT DOCUMENTS

| | | |
|---|---|---|
| 5,462,946 A | 10/1995 | Mitchell et al. |
| 5,700,654 A | 12/1997 | Roberts et al. |
| 5,885,857 A | 3/1999 | Yamaha et al. |
| 5,985,857 A | 11/1999 | Hudson et al. |
| 6,228,858 B1 | 5/2001 | Khalifah et al. |
| 6,342,500 B1 | 1/2002 | Khalifah et al. |
| 6,436,969 B1 | 8/2002 | Khalifah et al. |
| 6,610,852 B2 | 8/2003 | Khalifah et al. |
| 6,716,858 B1 | 4/2004 | Khalifah et al. |
| 6,730,686 B1 | 5/2004 | Khalifah et al. |
| 6,740,668 B1 | 5/2004 | Khalifah et al. |
| 7,030,146 B2 | 4/2006 | Baynes et al. |
| 7,214,799 B2 | 5/2007 | Khalifah et al. |
| 2003/0017995 A1 | 1/2003 | Khalifah et al. |
| 2004/0122061 A1 | 6/2004 | Khalifah et al. |
| 2007/0161678 A1 | 7/2007 | Khalifah et al. |

FOREIGN PATENT DOCUMENTS

| | | |
|---|---|---|
| WO | 00/21516 | 4/2000 |
| WO | 00/23063 | 4/2000 |
| WO | 2004/019889 | 3/2004 |

OTHER PUBLICATIONS

Cameron, et al., (1989), Q. J. Exp. Physiol. vol. 74, pp. 917-926.
Cameron, et al., (1986), Exp. Neurol., vol. 92, pp. 757-761.
PCT/US2007/015415 International Search Report.

*Primary Examiner* — James O Wilson
*Assistant Examiner* — Ebenezer O Sackey
(74) *Attorney, Agent, or Firm* — McDonnell Boehnen Hulbert & Berghoff LLP

(57) ABSTRACT

The present invention provides compounds of the formula,

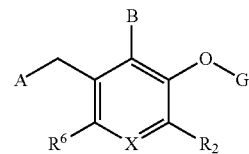

wherein A, B, G, $R^2$, $R^6$, and X are defined herein, pharmaceutical compositions of the same, and methods for treating or inhibiting development of AGE- and/or ALE-associated complications in subjects in need thereof.

20 Claims, 5 Drawing Sheets

FIGURE 1
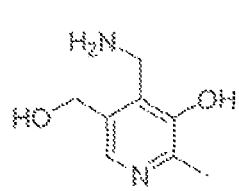
Pyridoxamine
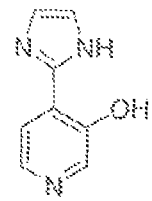
BST-4996
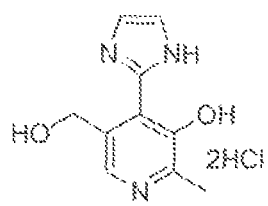
BST-4997
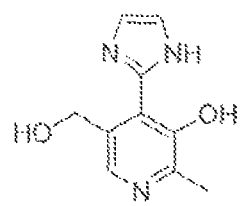
BST-198
(free base of BST-4997)
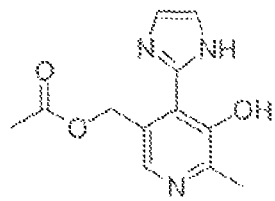
BST-146
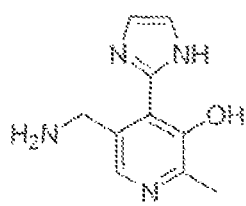
C-14521
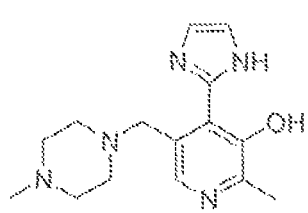
BST-605
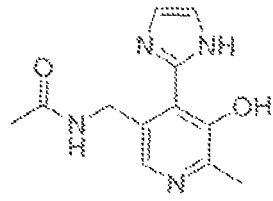
C-14547

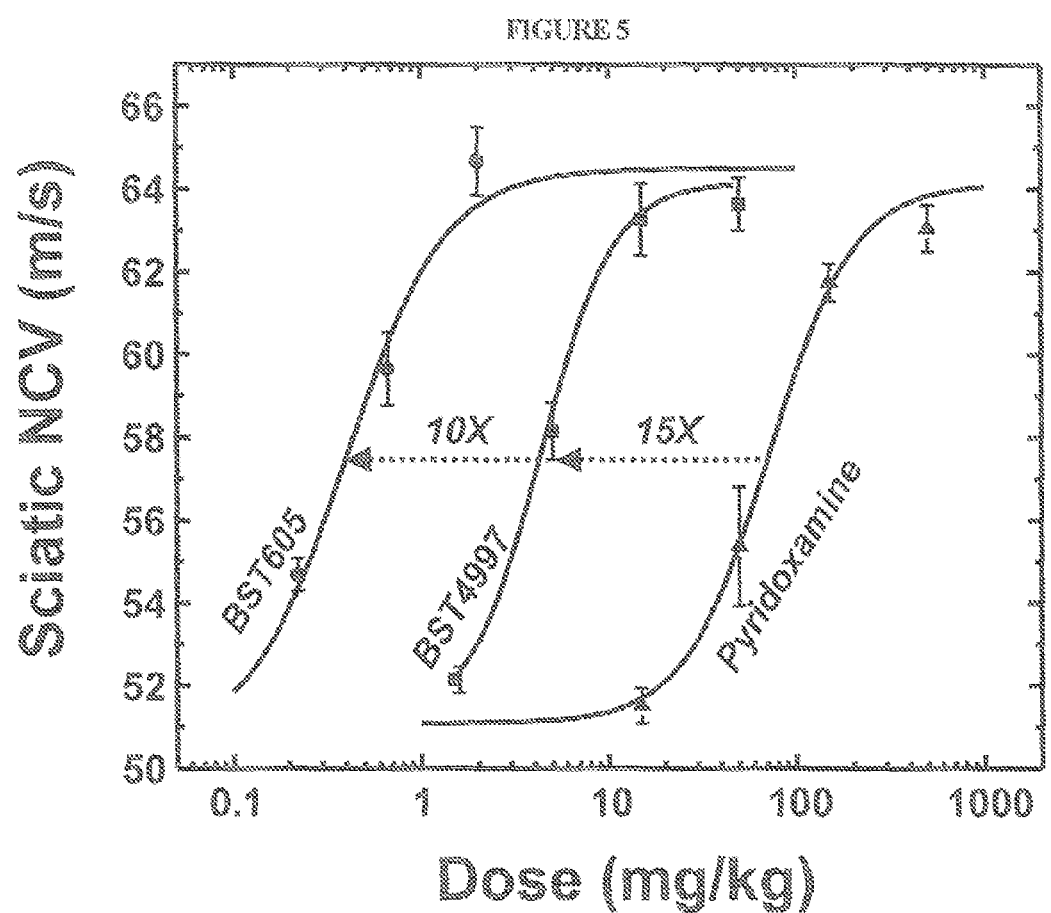

INHIBITORS OF ADVANCED GLYCATION END PRODUCTS

CROSS-REFERENCE

This application is a continuation to U.S. patent application Ser. No. 13/767,371, Feb. 14, 2013, which claims benefits to U.S. patent application Ser. No. 12/964,322 filed Dec. 9, 2010, which claims benefits to U.S. patent application Ser. No. 11/825,045 filed Jul. 3, 2007, which claims priority to Provisional Patent Application Ser. No. 60/819,437 filed Jul. 7, 2006, incorporated by reference herein in its entirety.

FIELD OF THE INVENTION

This application relates to the fields of chemistry, medicine, renal disease, vascular disease, hyperlipidemia, hyperglycemia, advanced glycation end-products, and advanced lipoxidation end-products.

BACKGROUND OF THE INVENTION

Advanced glycation end-products (AGEs) are carbohydrate-derived chemical modifications and crosslinks that accumulate in long-lived tissue proteins during normal aging. The increased rate of accumulation of AGEs during hyperglycemia is implicated in the development of long-term complications of diabetes, including but not limited to retinopathy, nephropathy, neuropathy, atherosclerosis, and cardiovascular disease. In addition, AGE formation has been implicated in a number of other pathologies, such as normal aging processes, arthritis, connective tissue disease, amyloidoses, and neurodegenerative amyloid diseases, such as Alzheimer's.

Advanced lipoxidation end products (ALEs) are lipid-derived chemical modifications and crosslinks that also accumulate in long-lived tissue proteins during normal aging, and are associated with hyperlipidemia, vascular disease, and renal disease in both diabetic and non-diabetic animal models. It is now recognized that some compounds, such as $N^\epsilon$-(carboxymethyl)lysine (CML) and $N^\epsilon$-(carboxyethyl)lysine (CEL), may be derived from either carbohydrates or lipids, leading to their designation as AGE/ALEs. Other compounds, such as pentosidine, appear to be true AGEs, while other compounds, such as malondialdehyde-lysine (MDA-Lys) and hydroxynonenal-lysine (HNE-Lys), are acknowledged to be ALEs, derived exclusively from lipids.

The elucidation of the pathogenic mechanisms of AGE and ALE-associated complications associated with hyperglycemia and/or hyperlipidemia is critical for developing rational therapy for their treatment and prevention. However, there is no consensus at present on the relative importance of the different possible pathogenic mechanisms that potentially contribute to these diabetic complications.

The compound pyridoxamine has recently been shown to inhibit both AGE and ALE formation in vitro, and to be useful for treating and preventing AGE and ALE-associated complications in hyperglycemic, hyperlipidemic, and hyperglycemic-hyperlipidemic animal models. (See, for example, U.S. Pat. No. 5,985,857; WO 00/21516; WO 00/23063) Such complications include, but are not limited to, diabetic nephropathy, proteinuria, impaired glomerular clearance, retinopathy, neuropathy, atherosclerosis, diabetes-associated hyperlipidemia, oxidative modification of proteins, urinary stone disease, obesity-related complications, proliferation or smooth muscle cells in the aorta, coronary artery occlusion, and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient.

However, there remains a need in the art for further options to treat or inhibit development of AGE- and ALE-associated complications in patients in need thereof, particularly patients with hyperglycemia and/or hyperlipidemia.

SUMMARY OF THE INVENTION

The present invention provides compounds, pharmaceutical compositions, and methods for treating or inhibiting development of AGE- and/or ALE-associated complications in a subject in need thereof. Thus, the invention provides novel compounds, detailed below, and pharmaceutical compositions thereof. In a preferred embodiment, the methods comprise administering one or more of the compounds or pharmaceutical compositions of the invention to subjects suffering from hyperglycemia and/or hyperlipidemia. The invention further comprises methods of treating or inhibiting development of disorders including diabetic nephropathy, proteinuria, impaired glomerular clearance, retinopathy, neuropathy, atherosclerosis, diabetes-associated hyperlipidemia, oxidative modification of proteins, arthritis, connective tissue diseases, amyloidosis, urinary stone disease, obesity-related complications, proliferation of smooth muscle cells in the aorta, coronary artery occlusion, and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient. Said methods comprise administering an effective amount of one or more compounds of the present invention, or a pharmaceutically acceptable salt thereof, to a subject in need of such treatment.

BRIEF DESCRIPTION OF THE FIGURES

FIG. 1 illustrates the chemical structures for several compounds referenced herein.

FIG. 5 is a graphical comparison of the effect of BST-605, BST-4997, and pyridoxamine on the restoration of nerve conduction velocity in motor (sciatic nerve) neurons in streptozotocin diabetic rats.

DETAILED DESCRIPTION OF THE INVENTION

Figure 2:
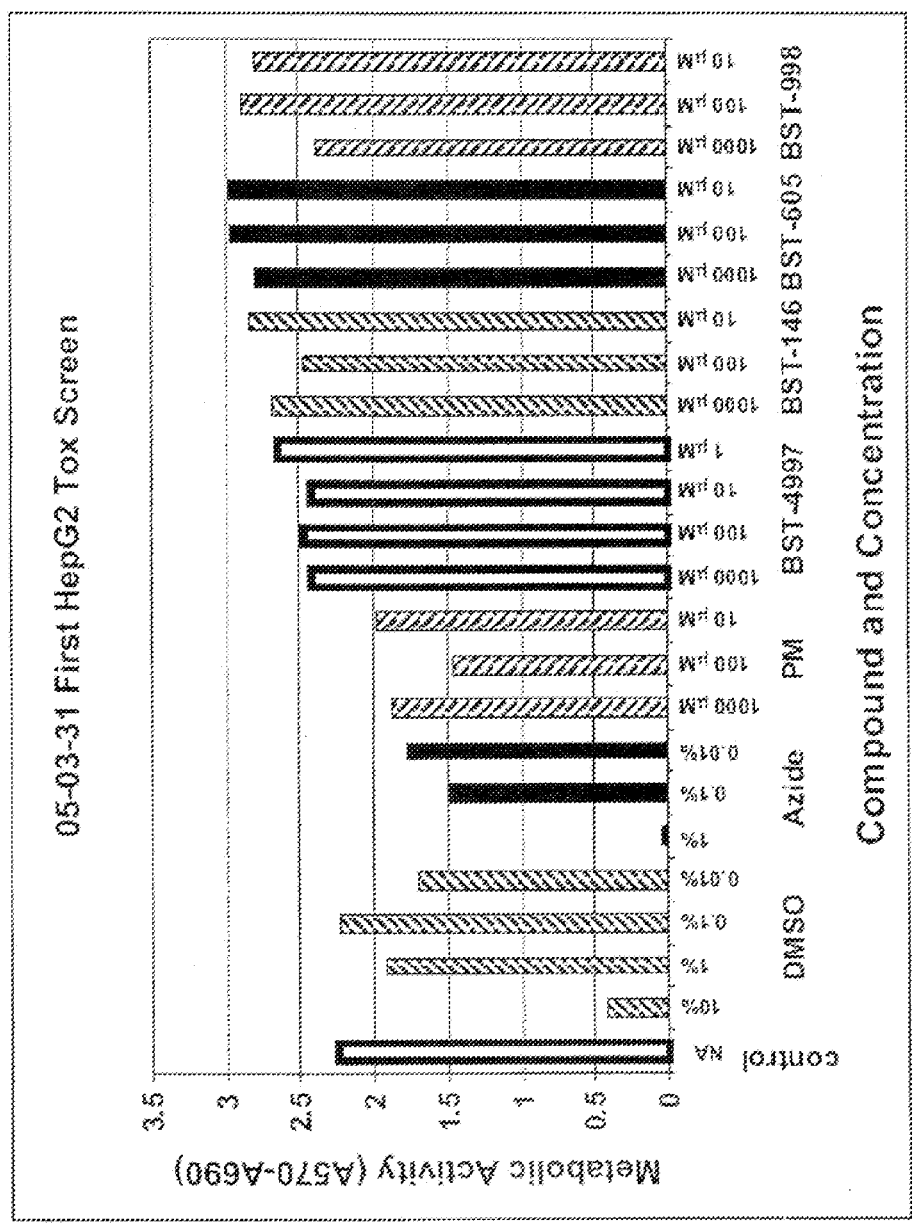
FIG. 2 is a graphical representation providing comparative cell toxicity data for pyridoxamine (PM), BST-4997, BST-998, BST-146, BST-605.

In a first aspect, the invention provides the compound of formula (I),

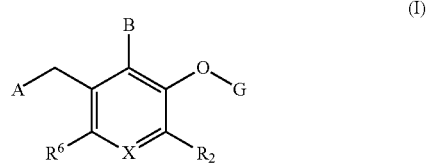

or a pharmaceutically acceptable salt thereof, wherein
X is N, N—O, or $CR^1$;
G is —H, heterocycle, or —$(C_1$-$C_6)$alkyl, wherein the heterocycle and alkyl are optionally substituted with at least one group independently selected from the group consisting of -halogen, —$OR^G$, —$N(R^G)_2$, —$SR^G$, —$S(O)R^G$, —$S(O)_2R^G$, —$COOR^G$, —$CON(R^G)_2$, and —$(C_1$-$C_6)$alkyl-$OR^G$, wherein $R^G$ is hydrogen, —$(C_1$-$C_6)$alkyl, or —$C(O)(C_1$-$C_6)$alkyl;
A is of formula (Ia),

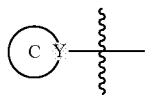

(Ia)

wherein
Y is N or N-oxide; and
ring C is:
(i) monocyclic;
(ii) saturated; and
(iii) contains 1 or 2 total heteroatoms, and 5 or 6 total atoms, wherein
the remaining heteroatom moiety is O, S, or $NR^{N1}$, and the carbon atoms are each optionally substituted with one or two $R^C$ wherein
$R^{N1}$ is —H, oxide, —$(C_1$-$C_6)$alkyl, —$(C_2$-$C_6)$alkenyl, —$(C_1$-$C_6)$alkynyl, —$(C_1$-$C_6)$haloalkyl, —$(C_1$-$C_6)$alkanoyl, —$(C_3$-$C_8)$cycloalkyl, -heterocycle, -aryl, -heteroaryl, —$(C_3$-$C_8)$cycloalkanoyl, -heterocycloyl, -aroyl, -heteroaroyl, —$(C_1$-$C_6)$alkoxycarbonyl, or -aryl$(C_1$-$C_6)$alkoxycarbonyl, wherein
$R^{N1}$ is optionally substituted with one or more groups which are independently -halogen, —$OR^{N12}$, —$N(R^{N12})_2$, —$COOR^{N12}$, —$CON(R^{N12})_2$, —$SR^{N12}$, —$S(O)R^{N12}$, —$S(O)_2R^{N12}$, —$NO_2$, —CN, —$(C_1$-$C_6)$alkyl, —$(C_1$-$C_6)$alkyl-$OR^{N12}$, -aryl, —$(C_1$-$C_6)$haloalkyl, —$(C_3$-$C_8)$cycloalkyl, —$(C_1$-$C_6)$alkanoyl, or -aroyl, wherein $R^{N12}$ is hydrogen, —$(C_1$-$C_6)$alkoxy, or —$C(O)(C_1$-$C_6)$alkyl;
each $R^C$ is independently —$Z^1$-M-$Z^2$—$R^2$, wherein
M is —C(O)—, —C(S)—, —S(O)—, —$S(O)_2$—, or absent,
provided when M is —S(O)—, —$S(O)_2$—, or absent, at least one of $Z^1$ and $Z^2$ is also absent;
$Z^1$ and $Z^2$ are independently —O—, —S—, —$N(R^N)$—, or absent, wherein
$R^N$ is —H, —$(C_1$-$C_6)$alkyl, —$(C_2$-$C_6)$alkenyl, —$(C_1$-$C_6)$alkynyl, —$(C_1$-$C_6)$haloalkyl, —$(C_1$-$C_6)$alkanoyl, —$(C_3$-$C_8)$cycloalkyl, -heterocycle, -aryl, -heteroaryl, —$(C_3$-$C_8)$cycloalkanoyl, -heterocycloyl, -aroyl, -heteroaroyl, —$(C_1$-$C_6)$alkoxycarbonyl, or -aryl$(C_1$-$C_6)$alkoxycarbonyl, wherein
$R^N$ is optionally substituted with one or more groups which are independently -halogen, —OR, —COOR, —$CONR_2$, —SR, —S(O)R, —$S(O)_2R$, —$NR_2$, —$NO_2$, —CN, —$(C_1$-$C_6)$alkyl, -aryl, -heterocycle, -heteroaryl, —$(C_3$-$C_8)$cycloalkyl, —$(C_1$-$C_6)$haloalkyl, —$(C_1$-$C_6)$alkanoyl, or -aroyl
wherein each R is independently —H, —$(C_1$-$C_6)$alkyl, —$(C_1$-$C_6)$haloalkyl, —$(C_1$-$C_6)$alkoxy, —$(C_3$-$C_8)$cycloalkyl, -heterocycloalkyl, aryl, or heteroaryl, wherein the alkyl and alkoxy are optionally substituted with one or more R';
wherein each R' is independently halogen, —OR'', —CN, —COR'', —COOR'', —CONR''$_2$, or NR''$_2$, wherein
each R'' is independently —H, —$(C_1$-$C_6)$alkyl, or —$(C_1$-$C_6)$haloalkyl;
$R^Z$ is —H, —$(C_1$-$C_6)$alkyl, —$(C_2$-$C_6)$alkenyl, —$(C_1$-$C_6)$alkynyl, —$(C_1$-$C_6)$haloalkyl, —$(C_3$-$C_8)$cycloalkyl, —$(C_1$-$C_6)$alkylaryl, -heterocycle, -aryl, or -heteroaryl, wherein
$R^Z$ is optionally substituted with at least one $R^{Z'}$, wherein
each $R^{Z'}$ is independently -halogen, —OR, —$(C_1$-$C_6)$alkoxy, —C(O)OR, —C(O)R, —$C(O)NR_2$, —$S(O)_2R$, —$OS(O)_2R$, -cyano, -nitro, —$(C_1$-$C_6)$alkyl, —$(C_1$-$C_6)$haloalkyl, —$(C_3$-$C_8)$cycloalkyl, -heterocycloalkyl, or heteroaryl,
wherein $R^{Z'}$ is optionally substituted with one or more R',
or any two $R^C$ attached to the same carbon, taken together, is oxo or =$N(R^{N4})$, wherein
$R^{N4}$ is —H, —OR, —$N(R^{N5})_2$, —$(C_1$-$C_6)$alkyl, —$(C_2$-$C_6)$alkenyl, —$(C_1$-$C_6)$alkynyl, —$(C_1$-$C_6)$haloalkyl, —$(C_1$-$C_6)$alkanoyl, —$(C_3$-$C_8)$cycloalkyl, -heterocycle, -aryl, or -heteroaryl, wherein
$R^{N4}$ is optionally substituted with one or more groups which are independently -halogen, —OH, -amino, —$(C_1$-$C_6)$alkylamino, —$(C_1$-$C_6)$dialkylamino, —$NO_2$, —CN, —$(C_1$-$C_6)$alkyl, -aryl, -heteroaryl, -heterocycle, —$(C_3$-$C_8)$cycloalkyl, —$(C_1$-$C_6)$haloalkyl, —$(C_1$-$C_6)$alkoxy, —$(C_1$-$C_6)$alkanoyl, or -aroyl; and
each $R^{N5}$ is independently —H, —$(C_1$-$C_6)$alkyl, —$(C_2$-$C_6)$alkenyl, —$(C_1$-$C_6)$alkynyl, —$(C_1$-$C_6)$haloalkyl, —$(C_1$-$C_6)$alkanoyl, or —$(C_3$-$C_8)$cycloalkyl;
B is of formula (Ib),

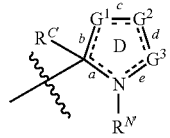

(Ib)

wherein
ring D is (i) monocyclic, and
(ii) saturated, unsaturated, or aromatic;
$R^{C'}$ is $R^C$, provided that $R^{C'}$ is not aryl or heteroaryl;
$G^1$, $G^2$, and $G^3$ each are independently N, O, $CR^3$, $C(R^3)_2$, or $NR^N$, wherein
each $R^3$ is independently —$Z^3$-M-$Z^4$—$R^Z$,
provided when M is —S(O)—, —$S(O)_2$—, or absent, at least one of $Z^3$ and $Z^4$ is also absent;
$Z^3$ and $Z^4$ are independently —O—, —S—, —$N(R^{N3})$— or absent, wherein
$R^{N3}$ is —H, —$(C_1$-$C_6)$alkyl, —$(C_2$-$C_6)$alkenyl, —$(C_1$-$C_6)$alkynyl, —$(C_1$-$C_6)$haloalkyl, —$(C_1$-$C_6)$alkanoyl, —$(C_3$-$C_8)$cycloalkanoyl, -heterocycloyl, -aroyl, -heteroaroyl, —$(C_1$-$C_6)$alkoxycarbonyl, or -aryl$(C_1$-$C_6)$alkoxycarbonyl, wherein $R^{N3}$ is optionally substituted with one or more groups which are independently -halogen, —OH, -amino, —($C_1$-$C_6$)alkylamino, —($C_1$-$C_6$)dialkylamino, —$NO_2$, —CN, —($C_1$-$C_6$)alkyl, -aryl, -heterocycle, -heteroaryl, —($C_3$-$C_8$)cycloalkyl, —($C_1$-$C_6$)haloalkyl, —($C_1$-$C_6$)alkoxy, —($C_1$-$C_6$)alkanoyl, or -aroyl;

or two $R^3$ taken together are oxo; and bonds a, b, c, d, and e are independently a single or double bond, provided that (i) no two consecutive atoms in ring D are both oxygen;
(ii) no two consecutive bonds are both double bonds;
(iii) if a or b is a double bond, then $R^{C'}$ is absent; and
(iv) if a or e is a double bond, then $R^{N'}$ is absent; and $R^1$, $R^2$, and $R^6$ are independently —H, -halogen, —$NO_2$, —CN, or $R^C$, provided that when X=$CR^1$, (i) $R^2$, $R^6$, and $R^{N1}$ are not phenyl;
(ii) $R^C$ is not aryl, heteroaryl, heterocycle, or ($C_2$-$C_6$) alkenyl
(iii) and $G^1$=N together, then $G^2$ is not O; and
(iv) two $R^C$ together may not form oxo;

and provided that when X=N, and (i) $G^1$ and $G^3$ each are $CR^3$, $G^2$=N, and bonds b and d are each a double bond, all simultaneously; or
(ii) $G^1$ is $CR^3$, $G^3$ is C(O), $G^2$ is $NR^{N'}$, and bond b is a double bond, all simultaneously;

either $R^2$ or $R^6$ is not —NH-aryl or —NH-heteroaryl.

In a preferred embodiment, the invention provides the compound according to formula (I) wherein G is hydrogen.

In a preferred embodiment, the invention provides the compound according to formula (I) wherein G is a heterocycle or —($C_1$-$C_6$)alkyl, each optionally substituted with at least one group independently selected from the group consisting of —$OR^G$, —N($R^G$)$_2$, —$SR^G$, —S(O)$R^G$, —S(O)$_2R^G$, —COO$R^G$, —CON($R^G$)$_2$, and —($C_1$-$C_6$)alkyl-$OR^G$, wherein $R^G$ is hydrogen, —($C_1$-$C_6$)alkyl, or —C(O)($C_1$-$C_6$)alkyl.

In another embodiment, the invention provides the compound according to formula (I), wherein X is N.

In another embodiment, the invention provides the compound according to formula (I), wherein X is N; and G is —H.

In another embodiment, the invention provides the compound according to formula (I), wherein X is N; and G is a heterocycle or —($C_1$-$C_6$)alkyl, each optionally substituted with at least one group independently selected from the group consisting of —$OR^G$, —N($R^G$)$_2$, —$SR^G$, —S(O)$R^G$, —S(O)$_2R^G$, —COO$R^G$, —CON($R^G$)$_2$, and —($C_1$-$C_6$)alkyl-$OR^G$, wherein $R^G$ is hydrogen, —($C_1$-$C_6$)alkyl, or —C(O)($C_1$-$C_6$)alkyl.

In another embodiment, the invention provides the compound according to formula (I), wherein X is N; and G is a heterocycle or —($C_1$-$C_6$)alkyl, each optionally substituted with at least one group independently selected from the group consisting of —OH and —COOH.

In another embodiment, the invention provides the compound according to formula (I), wherein X is N; and G is a tetrahydrofuranyl, tetrahydropyranyl, or —($C_5$-$C_6$)alkyl, each optionally substituted with at least one group independently selected from the group consisting of —OH and —COOH.

In another embodiment, the invention provides the compound according to formula (I), wherein X is N—O.

In another embodiment, the invention provides the compound according to formula (I), wherein X is N; G is hydrogen; B is aromatic; and $G^1$, $G^2$, and $G^3$ are each independently O, N or $CR^3$.

In preferred embodiment, the invention provides the compound according to formula (I), wherein X is N; G is hydrogen; and B is imidazolyl, oxazoyl, pyrazoyl, pyrroyl, or isoxazoyl wherein each carbon atom is substituted by $R^3$.

In more preferred embodiment, the invention provides the compound according to formula (I), wherein X is N; G is hydrogen; and B is imidazolyl, wherein each carbon atom is substituted by $R^3$.

In another embodiment, the invention provides the compound according to formula (I), wherein X is N; G is hydrogen;

B is imidazolyl, wherein each carbon atom is substituted by $R^3$; and wherein each $R^3$ is independently $R^{Z3}$, wherein
$R^{Z3}$ is —H, —($C_1$-$C_6$)alkyl, —($C_1$-$C_6$)haloalkyl, —($C_3$-$C_8$)cycloalkyl, —($C_1$-$C_6$)alkylaryl, -heterocycle, -aryl, or -heteroaryl, wherein $R^{Z3}$ is optionally substituted with at least one $R^{Z3'}$, wherein each $R^{Z3'}$ is independently -halogen, -cyano, —OR, —C(O)OR, —C(O)R, —C(O)$NR_2$, —($C_1$-$C_6$)alkyl, —($C_1$-$C_6$)haloalkyl, —($C_3$-$C_8$)cycloalkyl, or -heterocycloalkyl.

In another embodiment, the invention provides the compound according to formula (I), wherein X is N; G is hydrogen;

B is imidazolyl, wherein each carbon atom is substituted by $R^3$; and $R^2$ and $R^6$ are each —H, -halogen, —$NO_2$, —CN, or —$R^{Z6}$ wherein $R^{Z6}$ is —($C_1$-$C_6$)alkyl, —($C_1$-$C_6$)haloalkyl, —($C_3$-$C_8$)cycloalkyl, —($C_1$-$C_6$)alkylaryl, -heterocycle, -aryl, or -heteroaryl, wherein $R^{Z6}$ is optionally substituted with at least one $R^{Z6'}$, wherein each $R^{Z6'}$ is independently -halogen, —OR, —C(O)OR, —C(O)R, —($C_1$-$C_6$)alkyl, or —($C_1$-$C_6$)haloalkyl, wherein $R^{Z6'}$ is optionally substituted with one or more R'.

In another embodiment, the invention provides the compound according to formula (I), wherein X is N; G is hydrogen;

B is imidazolyl, wherein each carbon atom is substituted by $R^3$; and $R^{N'}$ is —H, —($C_1$-$C_6$)alkyl, —($C_1$-$C_6$)haloalkyl, —($C_1$-$C_6$)alkanoyl, —($C_3$-$C_8$)cycloalkyl, -aryl, -heteroaryl, —($C_3$-$C_8$)cycloalkanoyl, -heterocycloyl, -aroyl, -heteroaroyl, —($C_1$-$C_6$)alkoxycarbonyl, or -aryl($C_1$-$C_6$)alkoxycarbonyl, wherein $R^{N'}$ is optionally substituted with one or more groups which are independently -halogen, —$OR^{N''}$, —$NR^{N''}_2$, —$NO_2$, —CN, —($C_1$-$C_6$)alkyl, -aryl, -heterocycle, -heteroaryl, —($C_3$-$C_8$)cycloalkyl, or —($C_1$-$C_6$)haloalkyl, wherein each $R^{N''}$ is independently —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl, wherein the alkyl and alkoxy are optionally substituted with one or more R'.

In another embodiment, the invention provides the compound according to formula (I), wherein X is N; G is hydrogen;

B is imidazolyl, wherein each carbon atom is substituted by $R^3$;

Y is N; and ring C contains 2 heteroatoms, and 5 total atoms, wherein the remaining heteroatom moiety is O, S, or $NR^{N1}$, and the carbon atoms are each optionally substituted with one or two $R^C$.

In another embodiment, the invention provides the compound according to formula (I), wherein X is N; G is hydrogen;

B is imidazolyl, wherein each carbon atom is substituted by $R^3$;

Y is N; and ring C contains 2 heteroatoms, and 6 total atoms, wherein the remaining heteroatom moiety is O, S, or $NR^{N1}$, and the carbon atoms are each optionally substituted with one or two $R^C$.

In another embodiment, the invention provides the compound according to formula (I), wherein X is N; G is hydrogen;

B is not aromatic; and $G^1$, $G^2$, and $G^3$ are each independently O, N, $CR^3$, $C(R^3)_2$, or $N(R^{N'})$.

In a preferred embodiment, the invention provides the compound according to formula (I), wherein X is N; G is hydrogen;

B is pyrrolidinyl, pyrazolidinyl, imidazolidinyl, isoxazolidinyl, oxazolidinyl, triazolidinyl, or tetrazolidinyl, wherein each carbon is substituted by two $R^3$ and each nitrogen is substituted by $R^{N'}$.

In a more preferred embodiment, the invention provides the compound according to formula (I), wherein X is N; G is hydrogen;

B is pyrrolidinyl, pyrazolidinyl, imidazolidinyl, isoxazolidinyl, oxazolidinyl, triazolidinyl, or tetrazolidinyl, wherein each carbon is substituted by two $R^3$ and each nitrogen is substituted by $R^{N'}$; and each $R^3$ is independently $R^{Z3}$, wherein $R^{Z3}$ is —H, —$(C_1$-$C_6)$alkyl, —$(C_1$-$C_6)$haloalkyl, —$(C_3$-$C_8)$cycloalkyl, —$(C_1$-$C_6)$alkylaryl, -heterocycle, -aryl, or -heteroaryl, wherein $R^{Z3}$ is optionally substituted with at least one $R^{Z3'}$, wherein each $R^{Z3'}$ is independently -halogen, -cyano, —OR, —C(O)OR, —C(O)R, —C(O)$NR_2$, —$(C_1$-$C_6)$alkyl, —$(C_1$-$C_6)$haloalkyl, —$(C_3$-$C_8)$cycloalkyl, or -heterocycloalkyl.

In another embodiment, the invention provides the compound according to formula (I), wherein X is N; G is hydrogen;

B is pyrrolidinyl, pyrazolidinyl, imidazolidinyl, isoxazolidinyl, oxazolidinyl, triazolidinyl, or tetrazolidinyl, wherein each carbon is substituted by two $R^3$ and each nitrogen is substituted by $R^{N'}$; and $R^2$ and $R^6$ are each —H, -halogen, —$NO_2$, —CN, or —$R^{Z6}$ wherein $R^{Z6}$ is —$(C_1$-$C_6)$alkyl, —$(C_1$-$C_6)$haloalkyl, —$(C_3$-$C_8)$cycloalkyl, —$(C_1$-$C_6)$alkylaryl, -heterocycle, -aryl, or -heteroaryl, wherein $R^{Z6}$ is optionally substituted with at least one $R^{Z6'}$, wherein each $R^{Z6'}$ is independently -halogen, —OR, —C(O)OR, —C(O)R, —$(C_1$-$C_6)$alkyl, or —$(C_1$-$C_6)$haloalkyl, wherein $R^{Z6'}$ is optionally substituted with one or more R'.

In another embodiment, the invention provides the compound according to formula (I), wherein X is N; G is hydrogen;

B is pyrrolidinyl, pyrazolidinyl, imidazolidinyl, isoxazolidinyl, oxazolidinyl, triazolidinyl, or tetrazolidinyl, wherein each carbon is substituted by two $R^3$ and each nitrogen is substituted by $R^{N'}$; and each $R^{N'}$ is —H, —$(C_1$-$C_6)$alkyl, —$(C_1$-$C_6)$haloalkyl, —$(C_1$-$C_6)$alkanoyl, —$(C_3$-$C_8)$cycloalkyl, -aryl, -heteroaryl, —$(C_3$-$C_8)$cycloalkanoyl, -heterocycloyl, -aroyl, -heteroaroyl, —$(C_1$-$C_6)$alkoxycarbonyl, or -aryl $(C_1$-$C_6)$alkoxycarbonyl, wherein $R^{N'}$ is optionally substituted with one or more groups which are independently -halogen, —$OR^{N''}$, —$NR^{N''}_2$, —$NO_2$, —CN, —$(C_1$-$C_6)$alkyl, -aryl, -heterocycle, -heteroaryl, —$(C_3$-$C_8)$cycloalkyl, or —$(C_1$-$C_6)$haloalkyl, wherein each RN is independently —H, —$(C_1$-$C_6)$alkyl, —$(C_1$-$C_6)$haloalkyl, —$(C_1$-$C_6)$alkoxy, —$(C_3$-$C_8)$cycloalkyl, -heterocycloalkyl, aryl, or heteroaryl, wherein the alkyl and alkoxy are optionally substituted with one or more R'.

In another embodiment, the invention provides the compound according to formula (I), wherein X is N; G is hydrogen;

B is pyrrolidinyl, pyrazolidinyl, imidazolidinyl, isoxazolidinyl, oxazolidinyl, triazolidinyl, or tetrazolidinyl, wherein each carbon is substituted by two $R^3$ and each nitrogen is substituted by $R^{N'}$;

Y is N; and ring C contains 2 heteroatoms, and 5 total atoms, wherein the remaining heteroatom moiety is O, S, or $NR^{N1}$, and the carbon atoms are each optionally substituted with one or two $R^C$.

In another embodiment, the invention provides the compound according to formula (I), wherein X is N; G is hydrogen;

B is pyrrolidinyl, pyrazolidinyl, imidazolidinyl, isoxazolidinyl, oxazolidinyl, triazolidinyl, or tetrazolidinyl, wherein each carbon is substituted by two $R^3$ and each nitrogen is substituted by $R^{N'}$;

Y is N; and ring C contains 2 heteroatoms, and 6 total atoms, wherein the remaining heteroatom moiety is O, S, or $NR^{N1}$, and the carbon atoms are each optionally substituted with one or two $R^C$.

In another embodiment, the invention provides the compound according to formula (I), wherein X is $CR^1$.

In another embodiment, the invention provides the compound according to formula (I), wherein X is $CR^1$; and G is —H.

In another embodiment, the invention provides the compound according to formula (I), wherein X is $CR^1$; and G is a heterocycle or —$(C_1$-$C_6)$alkyl, each optionally substituted with at least one group independently selected from the group consisting of —$OR^G$, —$N(R^G)_2$, —$SR^G$, —$S(O)R^G$, —$S(O)_2R^G$, —$COOR^G$, —$CON(R^G)_2$, and —$(C_1$-$C_6)$alkyl-$OR^G$, wherein $R^G$ is hydrogen, —$(C_1$-$C_6)$alkyl, or —C(O)$(C_1$-$C_6)$alkyl.

In another embodiment, the invention provides the compound according to formula (I), wherein X is $CR^1$; and G is a heterocycle or —$(C_1$-$C_6)$alkyl, each optionally substituted with at least one group independently selected from the group consisting of —OH and —COOH.

In another embodiment, the invention provides the compound according to formula (I), wherein X is $CR^1$; and G is a tetrahydrofuranyl, tetrahydropyranyl, or —$(C_5$-$C_6)$alkyl, each optionally substituted with at least one group independently selected from the group consisting of —OH and —COOH.

In another embodiment, the invention provides the compound according to formula (I), wherein G is hydrogen; X is $CR^1$, wherein
- $R^1$ is —CN, —$NO_2$, -halogen, —$C(O)OR^4$, —$C(O)R^4$, —$C(O)N(R^4)_2$, —$S(O)R^4$, —$S(O)_2R^4$, or —$S(O)_2N(R^4)_2$,
  wherein
    - each $R^4$ is independently —H, —$(C_1$-$C_6)$alkyl, —$(C_2$-$C_6)$alkenyl,
      —$(C_3$-$C_8)$cycloalkyl, —$(C_1$-$C_6)$alkylaryl, -heterocycle, -aryl, or -heteroaryl, wherein
        - $R^4$ is optionally substituted with at least one group, each of which are independently -halogen, —OH, —$(C_1$-$C_6)$alkoxy, —$C(O)R^{41}$, —$S(O)_2R^{41}$, —$OS(O)_2R^{41}$, -cyano, -nitro, —$(C_1$-$C_6)$alkyl, or —$(C_1$-$C_6)$haloalkyl,
          wherein $R^{41}$ is —H, —$(C_1$-$C_6)$alkyl, —$(C_1$-$C_6)$haloalkyl, —$(C_1$-$C_6)$alkoxy, —$(C_3$-$C_8)$cycloalkyl, -heterocycloalkyl, aryl, or heteroaryl.

In another embodiment, the invention provides the compound according to formula (I), wherein G is hydrogen; X is $CR^1$, wherein
- $R^1$ is —CN, —$NO_2$, -halogen, —$C(O)OR^4$, —$C(O)R^4$, —$C(O)N(R^4)_2$, —$S(O)R^4$, —$S(O)_2R^4$, or —$S(O)_2N(R^4)_2$,
  wherein
    - each $R^4$ is independently —H, —$(C_1$-$C_6)$alkyl, —$(C_2$-$C_6)$alkenyl,
      —$(C_3$-$C_8)$cycloalkyl, —$(C_1$-$C_6)$alkylaryl, -heterocycle, -aryl, or -heteroaryl, wherein
        - $R^4$ is optionally substituted with at least one group, each of which are independently -halogen, —OH, —$(C_1$-$C_6)$alkoxy, —$C(O)R^{41}$, —$S(O)_2R^{41}$, —$OS(O)_2R^{41}$, -cyano, -nitro, —$(C_1$-$C_6)$alkyl, or —$(C_1$-$C_6)$haloalkyl,
          wherein $R^{41}$ is —H, —$(C_1$-$C_6)$alkyl, —$(C_1$-$C_6)$haloalkyl, —$(C_1$-$C_6)$alkoxy, —$(C_3$-$C_8)$cycloalkyl, -heterocycloalkyl, aryl, or heteroaryl;
- B is aromatic; and
- $G^1$, $G^2$, and $G^3$ are each independently O, N or $CR^3$.

In a preferred embodiment, the invention provides the compound according to formula (I), wherein G is hydrogen; X is $CR^1$, wherein
- $R^1$ is —CN, —$NO_2$, -halogen, —$C(O)OR^4$, —$C(O)R^4$, —$C(O)N(R^4)_2$, —$S(O)R^4$, —$S(O)_2R^4$, or —$S(O)_2N(R^4)_2$,
  wherein
    - each $R^4$ is independently —H, —$(C_1$-$C_6)$alkyl, —$(C_2$-$C_6)$alkenyl,
      —$(C_3$-$C_8)$cycloalkyl, —$(C_1$-$C_6)$alkylaryl, -heterocycle, -aryl, or -heteroaryl, wherein
        - $R^4$ is optionally substituted with at least one group, each of which are independently -halogen, —OH, —$(C_1$-$C_6)$alkoxy, —$C(O)R^{41}$, —$S(O)_2R^{41}$, —$OS(O)_2R^{41}$, -cyano, -nitro, —$(C_1$-$C_6)$alkyl, or —$(C_1$-$C_6)$haloalkyl,
          wherein $R^{41}$ is —H, —$(C_1$-$C_6)$alkyl, —$(C_1$-$C_6)$haloalkyl, —$(C_1$-$C_6)$alkoxy, —$(C_3$-$C_8)$cycloalkyl, -heterocycloalkyl, aryl, or heteroaryl;
- B is imidazolyl, oxazoyl, pyrazoyl, pyrroyl, or isoxazoyl wherein each carbon atom is substituted by $R^3$.

In a more preferred embodiment, the invention provides the compound according to formula (I), wherein G is hydrogen; X is $CR^1$, wherein
- $R^1$ is —CN, —$NO_2$, -halogen, —$C(O)OR^4$, —$C(O)R^4$, —$C(O)N(R^4)_2$, —$S(O)R^4$, —$S(O)_2R^4$, or —$S(O)_2N(R^4)_2$,
  wherein
    - each $R^4$ is independently —H, —$(C_1$-$C_6)$alkyl, —$(C_2$-$C_6)$alkenyl,
      —$(C_3$-$C_8)$cycloalkyl, —$(C_1$-$C_6)$alkylaryl, -heterocycle, -aryl, or -heteroaryl, wherein
        - $R^4$ is optionally substituted with at least one group, each of which are independently -halogen, —OH, —$(C_1$-$C_6)$alkoxy, —$C(O)R^{41}$, —$S(O)_2R^{41}$, —$OS(O)_2R^{41}$, -cyano, -nitro, —$(C_1$-$C_6)$alkyl, or —$(C_1$-$C_6)$haloalkyl,
          wherein $R^{41}$ is —H, —$(C_1$-$C_6)$alkyl, —$(C_1$-$C_6)$haloalkyl, —$(C_1$-$C_6)$alkoxy, —$(C_3$-$C_8)$cycloalkyl, -heterocycloalkyl, aryl, or heteroaryl;
- B is imidazolyl wherein each carbon atom is substituted by $R^3$; and In another embodiment, the invention provides the compound according to formula (I), wherein G is hydrogen; X is $CR^1$, wherein
- $R^1$ is —CN, —$NO_2$, -halogen, —$C(O)OR^4$, —$C(O)R^4$, —$C(O)N(R^4)_2$, —$S(O)R^4$, —$S(O)_2R^4$, or —$S(O)_2N(R^4)_2$,
  wherein
    - each $R^4$ is independently —H, —$(C_1$-$C_6)$alkyl, —$(C_2$-$C_6)$alkenyl,
      —$(C_3$-$C_8)$cycloalkyl, —$(C_1$-$C_6)$alkylaryl, -heterocycle, -aryl, or -heteroaryl, wherein
        - $R^4$ is optionally substituted with at least one group, each of which are independently -halogen, —OH, —$(C_1$-$C_6)$alkoxy, —$C(O)R^{41}$, —$S(O)_2R^{41}$, —$OS(O)_2R^{41}$, -cyano, -nitro, —$(C_1$-$C_6)$alkyl, or —$(C_1$-$C_6)$haloalkyl,
          wherein $R^{41}$ is —H, —$(C_1$-$C_6)$alkyl, —$(C_1$-$C_6)$haloalkyl, —$(C_1$-$C_6)$alkoxy, —$(C_3$-$C_8)$cycloalkyl, -heterocycloalkyl, aryl, or heteroaryl;
- B is imidazolyl wherein each carbon atom is substituted by $R^3$;
- each $R^3$ is independently $R^{Z3}$, wherein
    - $R^{Z3}$ is —H, —$(C_1$-$C_6)$alkyl, —$(C_1$-$C_6)$haloalkyl, —$(C_3$-$C_8)$cycloalkyl, —$(C_1$-$C_6)$alkylaryl, -heterocycle, -aryl, or -heteroaryl, wherein $R^{Z3}$ is optionally substituted with at least one $R^{Z3'}$, wherein
        - each $R^{Z3'}$ is independently -halogen, -cyano, —OR, —C(O)OR, —C(O)R, —$C(O)NR_2$, —$(C_1$-$C_6)$alkyl, —$(C_1$-$C_6)$haloalkyl, —$(C_3$-$C_8)$cycloalkyl, or -heterocycloalkyl.

In another embodiment, the invention provides the compound according to formula (I), wherein G is hydrogen; X is $CR^1$, wherein
- $R^1$ is —CN, —$NO_2$, -halogen, —$C(O)OR^4$, —$C(O)R^4$, —$C(O)N(R^4)_2$, —$S(O)R^4$, —$S(O)_2R^4$, or —$S(O)_2N(R^4)_2$,
  wherein
    - each $R^4$ is independently —H, —$(C_1$-$C_6)$alkyl, —$(C_2$-$C_6)$alkenyl,
      —$(C_3$-$C_8)$cycloalkyl, —$(C_1$-$C_6)$alkylaryl, -heterocycle, -aryl, or -heteroaryl, wherein
        - $R^4$ is optionally substituted with at least one group, each of which are independently -halogen, —OH, —$(C_1$-$C_6)$alkoxy, —$C(O)R^{41}$, —$S(O)_2R^{41}$, —$OS(O)_2R^{41}$, -cyano, -nitro, —$(C_1$-$C_6)$alkyl, or —$(C_1$-$C_6)$haloalkyl, wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;

B is imidazolyl wherein each carbon atom is substituted by $R^3$; and $R^2$ and $R^6$ are each —H, -halogen, —$NO_2$, —CN, or —$R^{Z6}$ wherein $R^{Z6}$ is —($C_1$-$C_6$)alkyl, —($C_1$-$C_6$)haloalkyl, —($C_3$-$C_8$)cycloalkyl, —($C_1$-$C_6$)alkylaryl, -heterocycle, -aryl, or -heteroaryl, wherein $R^{Z6}$ is optionally substituted with at least one $R^{Z6'}$, wherein each $R^{Z6'}$ is independently -halogen, —OR, —C(O)OR, —C(O)R, —($C_1$-$C_6$)alkyl, or —($C_1$-$C_6$)haloalkyl, wherein $R^{Z6'}$ is optionally substituted with one or more R'.

In another embodiment, the invention provides the compound according to formula (I), wherein G is hydrogen; X is $CR^1$, wherein $R^1$ is —CN, —$NO_2$, -halogen, —C(O)$OR^4$, —C(O)$R^4$, —C(O)N($R^4$)$_2$, —S(O)$R^4$, —S(O)$_2R^4$, or —S(O)$_2$N($R^4$)$_2$, wherein each $R^4$ is independently —H, —($C_1$-$C_6$)alkyl, —($C_2$-$C_6$)alkenyl, —($C_3$-$C_8$)cycloalkyl, —($C_1$-$C_6$)alkylaryl, -heterocycle, -aryl, or -heteroaryl, wherein $R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl, wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;

B is imidazolyl wherein each carbon atom is substituted by $R^3$; and $R^{N'}$ is —H, —($C_1$-$C_6$)alkyl, —($C_1$-$C_6$)haloalkyl, —($C_1$-$C_6$)alkanoyl, —($C_3$-$C_8$)cycloalkyl, -aryl, -heteroaryl, —($C_3$-$C_8$)cycloalkanoyl, -heterocycloyl, -aroyl, -heteroaroyl, —($C_1$-$C_6$)alkoxycarbonyl, or -aryl($C_1$-$C_6$)alkoxycarbonyl, wherein $R^{N'}$ is optionally substituted with one or more groups which are independently -halogen, —$OR^{N''}$, —$NR^{N''}{}_2$, —$NO_2$, —CN, —($C_1$-$C_6$)alkyl, -aryl, -heterocycle, -heteroaryl, —($C_3$-$C_8$)cycloalkyl, or —($C_1$-$C_6$)haloalkyl, wherein each $R^{N''}$ is independently —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl, wherein the alkyl and alkoxy are optionally substituted with one or more R'.

In another embodiment, the invention provides the compound according to formula (I), wherein G is hydrogen; X is $CR^1$, wherein $R^1$ is —CN, —$NO_2$, -halogen, —C(O)$OR^4$, —C(O)$R^4$, —C(O)N($R^4$)$_2$, —S(O)$R^4$, —S(O)$_2R^4$, or —S(O)$_2$N($R^4$)$_2$, wherein each $R^4$ is independently —H, —($C_1$-$C_6$)alkyl, —($C_2$-$C_6$)alkenyl, —($C_3$-$C_8$)cycloalkyl, —($C_1$-$C_6$)alkylaryl, -heterocycle, -aryl, or -heteroaryl, wherein $R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl, wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;

B is imidazolyl wherein each carbon atom is substituted by $R^3$;

Y is N; and ring C contains 2 heteroatoms, and 5 total atoms, wherein the remaining heteroatom moiety is O, S, or $NR^{N1}$, and the carbon atoms are each optionally substituted with one or two $R^C$.

In another embodiment, the invention provides the compound according to formula (I), wherein G is hydrogen; X is $CR^1$, wherein $R^1$ is —CN, —$NO_2$, -halogen, —C(O)$OR^4$, —C(O)$R^4$, —C(O)N($R^4$)$_2$, —S(O)$R^4$, —S(O)$_2R^4$, or —S(O)$_2$N($R^4$)$_2$, wherein each $R^4$ is independently —H, —($C_1$-$C_6$)alkyl, —($C_2$-$C_6$)alkenyl, —($C_3$-$C_8$)cycloalkyl, —($C_1$-$C_6$)alkylaryl, -heterocycle, -aryl, or -heteroaryl, wherein $R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl, wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;

B is imidazolyl wherein each carbon atom is substituted by $R^3$;

Y is N; and ring C contains 2 heteroatoms, and 6 total atoms, wherein the remaining heteroatom moiety is O, S, or $NR^{N1}$, and the carbon atoms are each optionally substituted with one or two $R^C$.

In another embodiment, the invention provides the compound according to formula (I), wherein G is hydrogen; X is $CR^1$, wherein $R^1$ is —CN, —$NO_2$, -halogen, —C(O)$OR^4$, —C(O)$R^4$, —C(O)N($R^4$)$_2$, —S(O)$R^4$, —S(O)$_2R^4$, or —S(O)$_2$N($R^4$)$_2$, wherein each $R^4$ is independently —H, —($C_1$-$C_6$)alkyl, —($C_2$-$C_6$)alkenyl, —($C_3$-$C_8$)cycloalkyl, —($C_1$-$C_6$)alkylaryl, -heterocycle, -aryl, or -heteroaryl, wherein $R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl, wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;

B is not aromatic; and $G^1$, $G^2$, and $G^3$ are each independently O, N, $CR^3$, $C(R^3)_2$, or $N(R^{N'})$.

In a preferred embodiment, the invention provides the compound according to formula (I), wherein G is hydrogen; X is $CR^1$, wherein $R^1$ is —CN, —$NO_2$, -halogen, —C(O)$OR^4$, —C(O)$R^4$, —C(O)N($R^4$)$_2$, —S(O)$R^4$, —S(O)$_2R^4$, or —S(O)$_2$N($R^4$)$_2$, wherein
  each $R^4$ is independently —H, —($C_1$-$C_6$)alkyl, —($C_2$-$C_6$)alkenyl,
    —($C_3$-$C_8$)cycloalkyl, —($C_1$-$C_6$)alkylaryl, -heterocycle, -aryl, or -heteroaryl, wherein
      $R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl,
        wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;
  B is pyrrolidinyl, pyrazolidinyl, imidazolidinyl, isoxazolidinyl, oxazolidinyl, triazolidinyl, or tetrazolidinyl, wherein
    each carbon is substituted by two $R^3$ and each nitrogen is substituted by $R^{N'}$.

In a more preferred embodiment, the invention provides the compound according to formula (I), wherein G is hydrogen; X is $CR^1$, wherein
  $R^1$ is —CN, —NO$_2$, -halogen, —C(O)O$R^4$, —C(O)$R^4$, —C(O)N($R^4$)$_2$, —S(O)$R^4$, —S(O)$_2R^4$, or —S(O)$_2$N($R^4$)$_2$,
  wherein
    each $R^4$ is independently —H, —($C_1$-$C_6$)alkyl, —($C_2$-$C_6$)alkenyl,
      —($C_3$-$C_8$)cycloalkyl, —($C_1$-$C_6$)alkylaryl, -heterocycle, -aryl, or -heteroaryl, wherein
        $R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl,
          wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;
  B is pyrrolidinyl, pyrazolidinyl, imidazolidinyl, isoxazolidinyl, oxazolidinyl, triazolidinyl, or tetrazolidinyl, wherein
    each carbon is substituted by two $R^3$ and each nitrogen is substituted by $R^{N'}$; and
  each $R^3$ is independently $R^{Z3}$, wherein
    $R^{Z3}$ is —H, —($C_1$-$C_6$)alkyl, —($C_1$-$C_6$)haloalkyl, —($C_3$-$C_8$)cycloalkyl, —($C_1$-$C_6$)alkylaryl, -heterocycle, -aryl, or -heteroaryl, wherein $R^{Z3}$ is optionally substituted with at least one $R^{Z3'}$, wherein
      each $R^{Z3'}$ is independently -halogen, -cyano, —OR, —C(O)OR, —C(O)R, —C(O)NR$_2$, —($C_1$-$C_6$)alkyl, —($C_1$-$C_6$)haloalkyl, —($C_3$-$C_8$)cycloalkyl, or -heterocycloalkyl.

In another embodiment, the invention provides the compound according to formula (I), wherein G is hydrogen; X is $CR^1$, wherein
  $R^1$ is —CN, —NO$_2$, -halogen, —C(O)O$R^4$, —C(O)$R^4$, —C(O)N($R^4$)$_2$, —S(O)$R^4$, —S(O)$_2R^4$, or —S(O)$_2$N($R^4$)$_2$,
  wherein
    each $R^4$ is independently —H, —($C_1$-$C_6$)alkyl, —($C_2$-$C_6$)alkenyl,
      —($C_3$-$C_8$)cycloalkyl, —($C_1$-$C_6$)alkylaryl, -heterocycle, -aryl, or -heteroaryl, wherein
        $R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl,
          wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;
  B is pyrrolidinyl, pyrazolidinyl, imidazolidinyl, isoxazolidinyl, oxazolidinyl, triazolidinyl, or tetrazolidinyl, wherein
    each carbon is substituted by two $R^3$ and each nitrogen is substituted by $R^{N'}$; and
  $R^2$ and $R^6$ are each —H, -halogen, —NO$_2$, —CN, or —$R^{Z6}$ wherein
    $R^{Z6}$ is —($C_1$-$C_6$)alkyl, —($C_1$-$C_6$)haloalkyl, —($C_3$-$C_8$)cycloalkyl, —($C_1$-$C_6$)alkylaryl, -heterocycle, -aryl, or -heteroaryl, wherein $R^{Z6}$ is optionally substituted with at least one $R^{Z6'}$,
      wherein each $R^{Z6'}$ is independently -halogen, —OR, —C(O)OR, —C(O)R, —($C_1$-$C_6$)alkyl, or —($C_1$-$C_6$)haloalkyl,
        wherein $R^{Z6'}$ is optionally substituted with one or more R'.

In a preferred embodiment, the invention provides the compound according to formula (I), wherein G is hydrogen; X is $CR^1$, wherein
  $R^1$ is —CN, —NO$_2$, -halogen, —C(O)O$R^4$, —C(O)$R^4$, —C(O)N($R^4$)$_2$, —S(O)$R^4$, —S(O)$_2R^4$, or —S(O)$_2$N($R^4$)$_2$,
  wherein
    each $R^4$ is independently —H, —($C_1$-$C_6$)alkyl, —($C_2$-$C_6$)alkenyl,
      —($C_3$-$C_8$)cycloalkyl, —($C_1$-$C_6$)alkylaryl, -heterocycle, -aryl, or -heteroaryl, wherein
        $R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl,
          wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;
  B is pyrrolidinyl, pyrazolidinyl, imidazolidinyl, isoxazolidinyl, oxazolidinyl, triazolidinyl, or tetrazolidinyl, wherein
    each carbon is substituted by two $R^3$ and each nitrogen is substituted by $R^{N'}$; and
  each $R^{N'}$ is independently —H, —($C_1$-$C_6$)alkyl, —($C_1$-$C_6$)haloalkyl, —($C_1$-$C_6$)alkanoyl, —($C_3$-$C_8$)cycloalkyl, -aryl, -heteroaryl, —($C_3$-$C_8$)cycloalkanoyl, -heterocycloyl, -aroyl, -heteroaroyl, —($C_1$-$C_6$)alkoxycarbonyl, or -aryl($C_1$-$C_6$)alkoxycarbonyl, wherein
    $R^{N'}$ is optionally substituted with one or more groups which are independently -halogen, —O$R^{N''}$, —N$R^{N''}{}_2$, —NO$_2$, —CN, —($C_1$-$C_6$)alkyl, -aryl, -heterocycle, -heteroaryl, —($C_3$-$C_8$)cycloalkyl, —($C_1$-$C_6$)haloalkyl,
      wherein each $R^{N''}$ is independently —H, —($C_1$-$C_6$)alkyl, —($C_1$-$C_6$)haloalkyl, —($C_1$-$C_6$)alkoxy, or —($C_3$-$C_8$)cycloalkyl, -heterocycloalkyl, aryl, or heteroaryl, wherein the alkyl and alkoxy are optionally substituted with one or more R'.

In a more preferred embodiment, the invention provides the compound according to formula (I), wherein G is hydrogen; X is $CR^1$, wherein
  $R^1$ is —CN, —NO$_2$, -halogen, —C(O)O$R^4$, —C(O)$R^4$, —C(O)N($R^4$)$_2$, —S(O)$R^4$, —S(O)$_2R^4$, or —S(O)$_2$N($R^4$)$_2$,
  wherein
    each $R^4$ is independently —H, —($C_1$-$C_6$)alkyl, —($C_2$-$C_6$)alkenyl, —($C_3$-$C_8$)cycloalkyl, —($C_1$-$C_6$)alkylaryl, -heterocycle, -aryl, or -heteroaryl, wherein
$R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl,
wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;
B is pyrrolidinyl, pyrazolidinyl, imidazolidinyl, isoxazolidinyl, oxazolidinyl, triazolidinyl, or tetrazolidinyl, wherein
each carbon is substituted by two $R^3$ and each nitrogen is substituted by $R^{N'}$;
Y is N; and
ring C contains 2 heteroatoms, and 5 total atoms, wherein the remaining heteroatom moiety is O, S, or $NR^{N1}$, and the carbon atoms are each optionally substituted with one or two $R^C$.

In another embodiment, the invention provides the compound according to formula (I), wherein G is hydrogen; X is $CR^1$, wherein
$R^1$ is —CN, —$NO_2$, -halogen, —C(O)$OR^4$, —C(O)$R^4$, —C(O)N($R^4$)$_2$, —S(O)$R^4$, —S(O)$_2R^4$, or —S(O)$_2$N($R^4$)$_2$,
wherein
each $R^4$ is independently —H, —($C_1$-$C_6$)alkyl, —($C_2$-$C_6$)alkenyl,
—($C_3$-$C_8$)cycloalkyl, —($C_1$-$C_6$)alkylaryl, -heterocycle, -aryl, or -heteroaryl, wherein
$R^4$ is optionally substituted with at least one group, each of which are independently -halogen, —OH, —($C_1$-$C_6$)alkoxy, —C(O)$R^{41}$, —S(O)$_2R^{41}$, —OS(O)$_2R^{41}$, -cyano, -nitro, —($C_1$-$C_6$)alkyl, or —($C_1$-$C_6$)haloalkyl,
wherein $R^{41}$ is —H, —($C_1$-$C_6$)alkyl, —($C_1$-$C_6$)haloalkyl, —($C_1$-$C_6$)alkoxy, —($C_3$-$C_8$)cycloalkyl, -heterocycloalkyl, aryl, or heteroaryl;
B is pyrrolidinyl, pyrazolidinyl, imidazolidinyl, isoxazolidinyl, oxazolidinyl, triazolidinyl, or tetrazolidinyl, wherein
each carbon is substituted by two $R^3$ and each nitrogen is substituted by $R^{N'}$;
Y is N; and
ring C contains 2 heteroatoms, and 6 total atoms, wherein the remaining heteroatom moiety is O, S, or $NR^{N1}$, and the carbon atoms are each optionally substituted with one or two $R^C$.

In another embodiment, the invention provides the compound according to formula (I), which is 4-(1H-imidazol-2-yl)-2-methyl-5-((4-methylpiperazin-1-yl)methyl)pyridin-3-ol.

In a further aspect, the present invention provides pharmaceutical compositions comprising one or more compounds of the invention, as disclosed above and a pharmaceutically acceptable carrier. Preferred embodiments of the pharmaceutical compositions are described below.

In a further aspect, the present invention provides methods for treating or inhibiting development of one or more AGE- and/or ALE-associated complications in subject in need thereof comprising administering one or more compounds or pharmaceutical compositions of the invention to a subject in need thereof. As used herein, the phrase "AGE and/or ALE associated complications" includes, but is not limited to accelerated protein aging, retinopathy, nephropathy, proteinuria, impaired glomerular clearance, neuropathy, hyperlipidemia, hypertriglyceridemia, hypercholesterolemia, atherosclerosis, cardiovascular disease, and neurodegenerative amyloid diseases, such as Alzheimer's disease, diabetes-associated hyperlipidemia, oxidative modification of proteins, arthritis, connective tissue diseases, amyloidosis, urinary stone disease, obesity-related complications proliferation or smooth muscle cells in the aorta, coronary artery occlusion, oxidative stress-related conditions, and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient.

In a further aspect, the invention provides methods for treating or inhibiting development of one or more of diabetic nephropathy, proteinuria, impaired glomerular clearance, retinopathy, neuropathy, atherosclerosis, diabetes-associated hyperlipidemia, oxidative modification of proteins, arthritis, connective tissue diseases, amyloidosis, urinary stone disease, obesity-related complications proliferation or smooth muscle cells in the aorta, coronary artery occlusion, oxidative stress-related disorders and hypertension; and dialysis-related disorders including dialysis-related cardiac morbidity and mortality, dialysis-related amyloidosis, dialysis-related increases in permeability of the peritoneal membrane in a dialysis patient, renal failure progression in a dialysis patient, and inhibiting ultrafiltration failure and peritoneal membrane destruction in a dialysis patient, wherein the methods comprise administering an effective amount of one or more compounds of the present invention, or a pharmaceutically acceptable salt thereof, to a subject in need of such treatment.

In a preferred embodiment, the methods are used to treat patients suffering from hyperlipidemia and/or hyperglycemia or their complications, or to inhibit development of complications arising from hyperlipidemia and/or hyperglycemia, such as those described above.

While the methods of this aspect of the present invention are not limited by a specific mechanism, it is believed that the compounds of the invention are useful in treating or inhibiting development of these complications based on their ability to inhibit AGE and/or ALE formation, and thus to inhibit the development or progression of complications associated with accumulation of AGEs and/or ALEs.

Definitions

As used herein, "treat" or "treating" means accomplishing one or more of the following: (a) reducing the severity of the disorder; (b) limiting or preventing development of symptoms characteristic of the disorders) being treated; (c) inhibiting worsening of symptoms characteristic of the disorders) being treated; (d) limiting or preventing recurrence of the disorders) in patients that have previously had the disorders); and (e) limiting or preventing recurrence of symptoms in patients that were previously symptomatic for the disorders).

As used herein, the term "inhibiting development of" means to prevent or to minimize development of the disorder or complication in individuals at risk of developing the disorder or complication.

The term "absent" as used herein means the group is replaced by a single bond. If replacing the group with a bond results in two connected moieties both defined as bonds, then -bond-bond- groups are understood to reduce to a single bond.

The term "alkenyl" as used herein, means a straight or branched chain hydrocarbon containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkanoyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means phenyl or a bicyclic aryl or a tricyclic aryl. The bicyclic aryl is naphthyl, or a phenyl fused to a cycloalkyl, or a phenyl fused to a cycloalkenyl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, azulenyl, dihydroanthracenyl, fluorenyl, andtetrahydrophenanthrenyl.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aroyl" as used herein, means an aryl group, as defined herein, appended to the parent molecular moiety through a carbonyl group, as defined herein. Representative examples of arylcarbonyl include, but are not limited to, benzoyl and naphthoyl.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The term "cycloalkanoyl" as used herein, means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The term "heteroaryloyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heterocycle" as used herein, means a monocyclic, and 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The heterocycle is connected to the parent molecular moiety through any carbon atom or any nitrogen atom contained within the monocyclic heterocycle. Representative examples of heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "heterocycloyl" as used herein, means a heterocycle, as defined herein, appended to the parent molecular moiety through a carbonyl group, as defined herein.

"Oxidative stress" is defined as specific increases in reactive oxygen species and derived free radicals. Oxidative-stress related conditions include, but are not limited to atherosclerosis, ischemia-reperfusion injury, inflammatory diseases such as arthritis, cancer, exposure to ionizing radiation and/or chemotherapeutic agents, pulmonary adult respiratory distress syndrome (ARDS), myocardial infarction and strokes, pancreatitis, or intestinal ulceration, and aging. (See, for example, U.S. Pat. Nos. 5,700,654 and 5,462,946).

The term "oxide" as used herein, means an —O moiety; for example, attachment of an oxide group to a nitrogen forms an N-oxide compound, as is familiar to those skilled in the art. In such compounds, the oxygen has a formal negative charge and the nitrogen has a formal positive charge, therefore, the entire compound has a zero net charge.

The term "oxo" as used herein, means an =O moiety.

Pharmaceutical Compositions and Administration

The instant compounds can be administered individually or in combination, usually in the form of a pharmaceutical composition. Such compositions are prepared in a manner well known in the pharmaceutical art and comprise at least one active compound.

The compounds of the invention can be administered as the sole active pharmaceutical agent, or they can be used in combination with one or more other compounds useful for carrying out the methods of the invention, including but not limited to pyridoxamine, aminoguanidine, compounds disclosed in WO 2004/019889 (including but not limited to BST 4996, BST 4997, and BST-146; agents that promote glycemic control, such as insulin, metformin, and thiazolidinediones; and anti-hypertensives such as angiotensin converting enzyme inhibitors (ACEI), angiotensin II receptor blockers (ARB), endothelin receptor antagonists and rennin inhibitors. When administered as a combination, the therapeutic agents can be formulated as separate compositions that are given at the same time or different times, or the therapeutic agents can be given as a single composition.

The compounds may be made up in a solid form (including granules, powders or suppositories) or in a liquid form (e.g., solutions, suspensions, or emulsions). The compounds of the invention may be applied in a variety of solutions and may be subjected to conventional pharmaceutical operations such as sterilization and/or may contain conventional adjuvants, such as preservatives, stabilizers, wetting agents, emulsifiers, buffers etc.

The compounds of the invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier. One or more compounds of the invention may be present in association with one or more non-toxic pharmaceutically acceptable carriers and/or diluents and/or adjuvants, and if desired other active ingredients. The pharmaceutical compositions containing compounds of the invention may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds and pharmaceutical compositions of the present invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds and pharmaceutical compositions of the present invention may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.01 mg to about 50 mg per kilogram of body weight per day, more preferably between 0.1 mg to about 50 mg per kilogram of body weight per day, and even more preferably between about 0.1 mg to about 20 mg per kilogram of body weight per day are useful in the treatment of the above-indicated conditions. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions containing the compounds described herein are administered to an individual in need thereof. In a preferred embodiment, the subject is a mammal; in a more preferred embodiment, the subject is a human. In therapeutic applications, compositions are administered in an amount sufficient to carry out the methods of the invention. Amounts effective for these uses depend on factors including, but not limited to, the nature of the compound (specific activity, etc.), the route of administration, the stage and severity of the disorder, the weight and general state of health of the subject, and the judgment of the prescribing physician. The active compounds are effective over a wide dosage range. However, it will be understood that the amount of the compound actually administered will be determined by a physician, in the light of the above relevant circumstances. Therefore, the above dosage ranges are not intended to limit the scope of the invention in any way.

For administration to non-human mammals, the composition may also be added to the animal feed or drinking water. It may be convenient to formulate these animal feed and drinking water compositions so that the animal ingests an appropriate quantity of the composition during a meal or throughout the course of the day. It may also be convenient to present the composition as a premix for addition to the feed or drinking water.

Preparation of Compounds of the Invention

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1999). Suitable protecting groups include, but are not limited to, tert-butoxycarbonyl (BOC), trimethylsilylethanesulfonamide (SES), benzyloxycarbonyl (CBZ) and benzyl (Bn) protecting groups.

Scheme 1

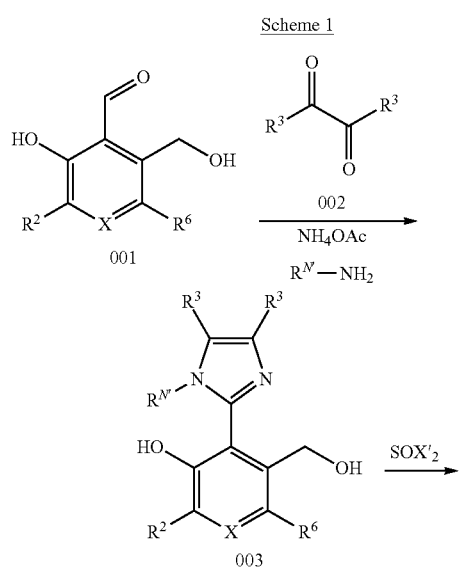

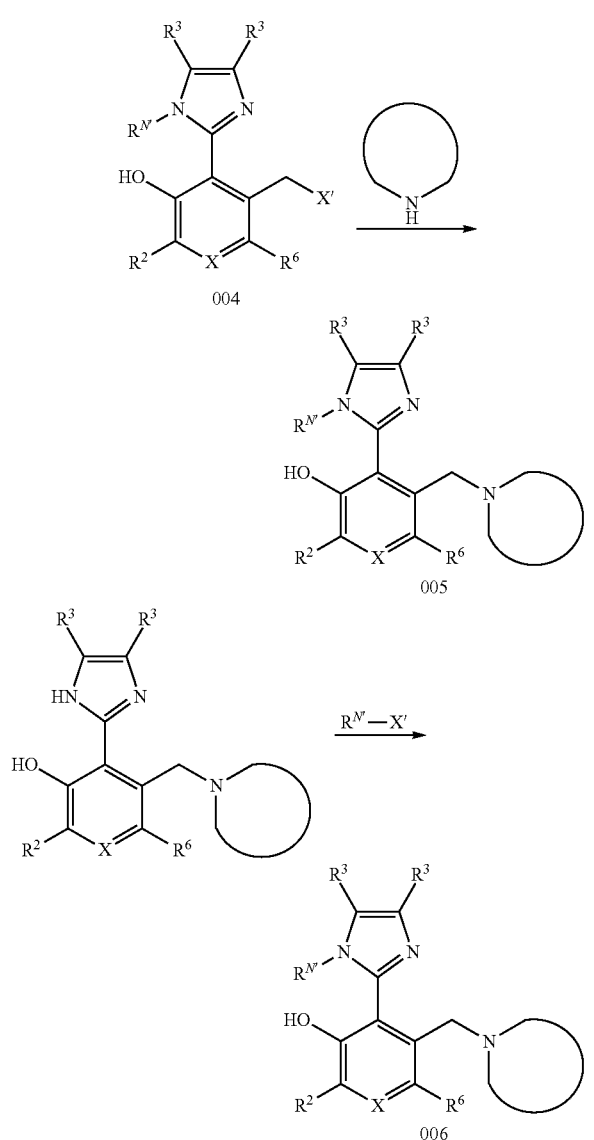

Scheme 2

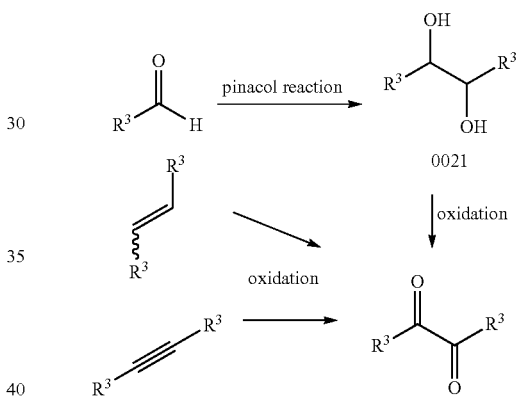

One possible procedure to prepare compounds of the invention is shown in Scheme 1. Imidazole compounds (003, $R^{N'}$=H) are synthesized by reaction of α-diketones (002) with pyridoxal hydrochloride (001) and a source of ammonia ($NH_4OAc$). If a primary amine ($R^{N'}-NH_2$) is included in the reaction, the N-functionalized product is formed. The hydroxymethyl of 003 is converted to the halomethyl derivative (004) with $SOCl_2$ (X'=Cl). Alternatively, reagents such as $POCl_3$, $PCl_5$, $PCl_3$, $PPh_3$ and $CCl_4$ (X'=Cl); $SOBr_2$, $PPh_3$ and $CBr_4$, $PPh_3$ and $Br_2$ (X'=Br); and $PPh_3$ and h or N-iodosuccinimide (X'=I) may be utilized. Subsequently, the substitution of the halomethyl derivative (004) with a cyclic amine yields 005. If the imidazole nitrogen is unsubstituted (005, $R^{N'}$=H), it may be further substituted by reaction with a reagent of the form $R^{N'}-X'$ or $R^{N'}-O-R^{N'}$ to yield compound 006. Examples of appropriate reagents include, but are not limited to $CH_3I$, $CF_3CH_2I$, $HOCH_2CH_2Br$, $CH_3(CO)Cl$, $(CF_3CO)O(COCF_3)$, $(PhCO)O(COPh)$, and the like.

α-Diketones (002, Scheme 1) can be prepared by methods familiar to those skilled in the art. A few techniques are summarized in Scheme 2, involving one or two step procedures. The desired α-diketones may be prepared directly from alkenes by reaction with reagents such as $KMnO_4$ in the presence of acetic anhydride or cupric sulfate. Alternatively, alkynes may be utilized with reagents such as $KMnO_4$ in the presence of acetic acid or $NaHCO_3$ with $MgSO_4$; $H_2O_2$ and $MeReO_3$; NaOCl or $NaIO_4$ and catalytic $RuO_2$; or PhIO and $RuCl_2(PPh_3)_2$. In two steps, symmetric or asymmetric (where two different aldehydes with different $R^3$ groups are used) α-diols (0021) may be prepared from the corresponding aldehydes through the pinacol reaction. Appropriate reagents for the pinacol reaction include, but are not limited to Li, Na, $TiCl_3$, Zn and HCl, and $SmI_2$. The α-diols (0021) may oxidized to the corresponding α-diketone (002) with acetic anhydride or trifluoroacetic anhydride in DMSO; or with NaOCl and catalytic 4-methoxy-2,2,6,6-tetramethyl-1-piperidinyloxy, free radical (4-methoxy-TEMPO).

Example 1

4-(4,5-Diethyl-1H-imidazol-2-yl)-5-hydroxymethyl-2-methyl-pyridin-3-ol

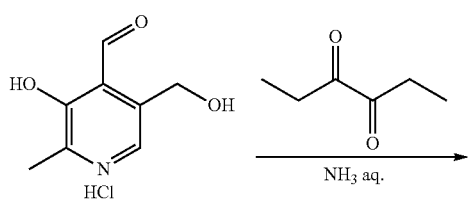

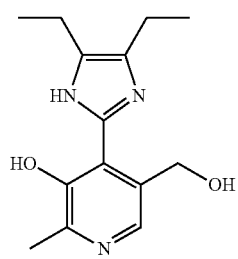

Pyridoxal hydrochloride (2.03 g, 10 mmol) was dissolved in MeOH (25 mL) and cooled to 0-5° C. 3,4-Hexanedione (8.4 mL, 70 mmol) was added at 0-5° C. and then aq. ammonium hydroxide solution (25%, 8 mL) keeping the temperature between 5-10° C. The reaction mixture was warmed to rt and stirred over a period of 15 h. The suspension was filtered and the filtrate was evaporated to distill off MeOH. Water (10 mL) was added and extracted with ethyl acetate (4×15 mL). The combined organic layers were washed with water (10 mL), brine (10 mL), dried over $Na_2SO_4$ (5 g) and evaporated to dryness. The residue was suspended in ethyl acetate (10 mL) and diethyl ether (20 mL) and stirred for 30 min. The suspension was filtered off, washed with diethyl ether (20 mL) and dried to give the title compound (920 mg) as yellow crystals.

Example 2

4-(4,5-Diphenyl-1H-imidazol-2-yl)-5-hydroxymethyl-2-methyl-pyridin-3-ol

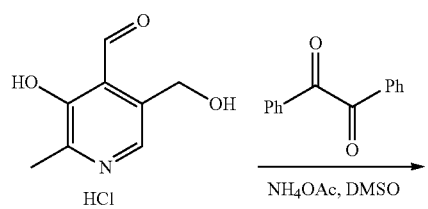

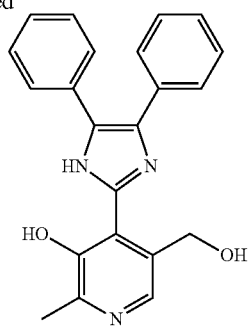

Benzil (2.10 g, 10 mmol), ammonium acetate (11.5 g, 150 mmol) were dissolved in DMSO (60 mL) and heated to 100° C. Pyridoxal hydrochloride (4.1 g, 20 mmol) in DMSO (50 mL) was added drop wise and after 100 min stirring at 100° C. the reaction mixture was poured into icewater (300 mL) and aq. ammonium hydroxide solution (50 mL). The precipitate was filtered off, washed with water (100 mL), dissolved in ethyl acetate (150 mL) and extracted with water (2×50 mL). The organic layer was dried over $MgSO_4$ (10 g) and evaporated to dryness. The residue was purified by flash chromatography on silica gel eluting with toluene/acetone 7/3. Fractions containing product were evaporated to a volume of 50 mL and cooled to 0° C. The precipitate was filtered off and dried to give (250 mg) the title compound as a yellow solid.

Example 3

4-[4,5-Bis-(4-fluoro-phenyl)-1H-imidazol-2-yl]-5-hydroxymethyl-2-methyl-pyridin-3-ol

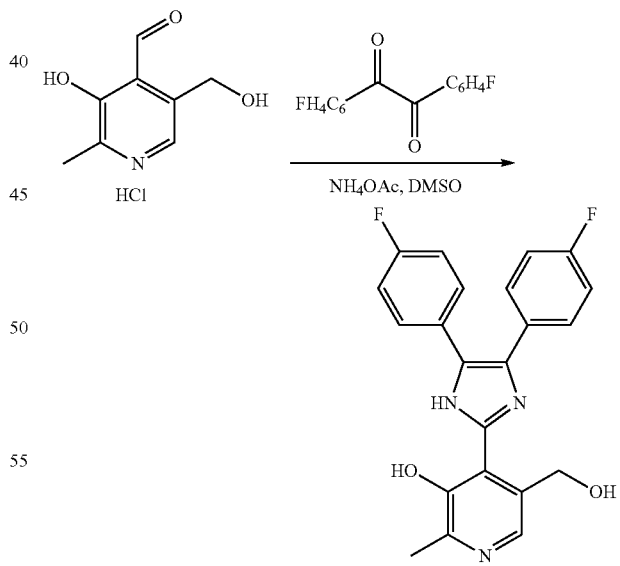

4,4'-Difluorobenzil (2.46 g, 10 mmol), ammonium acetate (11.5 g, 150 mmol) were dissolved in DMSO (60 mL) and heated to 100° C. Pyridoxal hydrochloride (6.1 g, 30 mmol) in DMSO (50 mL) was added drop wise over a period of 40 min. The reaction mixture was cooled to it and poured into icewater (300 mL) and aq. ammonium hydroxide solution (50 mL). The precipitate was filtered off, washed with water (100 mL), dissolved in ethyl acetate (150 mL) and extracted with water (2×50 mL). The organic layer was dried over MgSO₄ (10 g) and evaporated to dryness. The residue was purified by flash chromatography on silica gel eluting with toluene/acetone 7/3. Fractions containing product were evaporated to a volume of 50 mL and cooled to 0° C. The precipitate was filtered off and dried to give (250 mg) the title compound as a yellow solid.

Example 4

4-(4,5-Di-furan-2-yl-1H-imidazol-2-yl)-5-hydroxymethyl-2-methyl-pyridin-3-ol

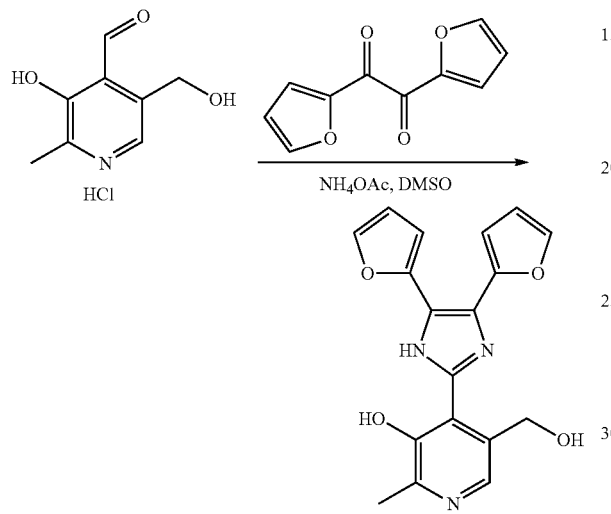

α-Fluril (1.90 g, 10 mmol), ammonium acetate (11.5 g, 150 mmol) were dissolved in DMSO (60 mL) and heated to 100° C. Pyridoxal hydrochloride (6.1 g, 30 mmol) in DMSO (50 mL) was added drop wise over a period of 35 min. The reaction mixture was cooled to rt and poured into icewater (300 mL) and aq. ammonium hydroxide solution (50 mL). The precipitate was filtered off, washed with water (100 mL), dissolved in ethyl acetate (3×200 mL) and extracted with water (50 mL). The organic layer was dried over MgSO₄ (5 g) and evaporated to dryness. The residue was purified by flash chromatography on silica gel eluting with toluene/acetone 7/3. Fractions 13-18 were evaporated to a volume of 20 mL, the precipitate was filtered off and dried to give (170 mg) a light beige solid. Fractions 19-44 were evaporated to a volume of 20 mL, the precipitate was filtered off and dried to give (320 mg) the title compound as a light beige solid.

Example 5

5-(Chloromethyl)-4-(1H-imidazol-2-yl)-2-methyl-pyridin-3-ol hydrochloride

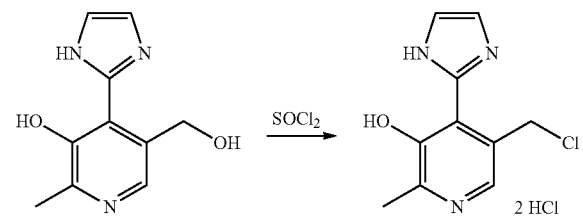

5-(hydroxymethyl)-4-(1H-imidazol-2-yl)-2-methylpyridin-3-ol (5.1 g, 25 mmol) was suspended in toluene (100 mL) and thionyl chloride (25 mL) was added. The suspension was heated to reflux for 2 h, cooled to 0° C. and filtered. The title compound was obtained as brown solid (Purity by NMR: 70-80%) and was used without further purification in the next step.

Example 6

4-(1H-Imidazol-2-yl)-2-methyl-5-[(4-methyl-1-piperazinyl)methyl-pyridin-3-ol

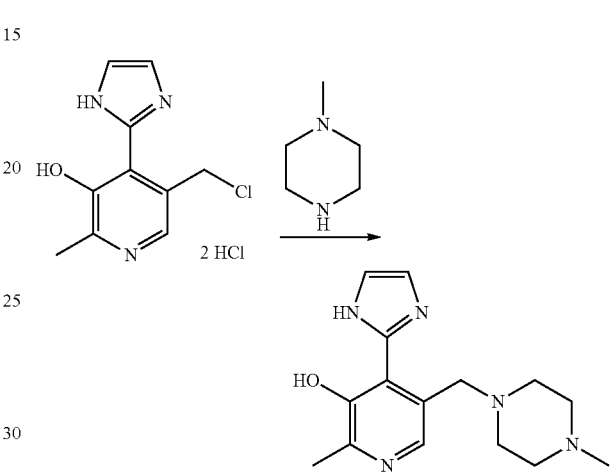

5-(chloromethyl)-4-(1H-imidazol-2-yl)-2-methylpyridin-3-ol hydrochloride (591 mg, 2 mmol) was suspended in methylene chloride (25 mL) and N-methyl piperazine (2.2 mL, 20 mmol) was added. After 20 h stirring at rt, the reaction mixture was evaporated to dryness. The residue was purified twice by chromatography on silica gel eluting with methylene chloride/methanol 9/1. The title compound (150 mg) was obtained as red brown oil.

Example 7

5-(Hydroxy-methyl)-2-methyl-4-(1-methyl-1H-imidazol-2-yl)-pyridin-3-ol

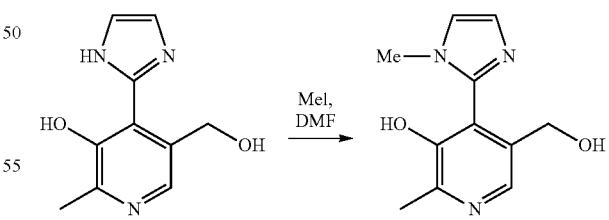

5-(hydroxymethyl)-4-(1H-imidazol-2-yl)-2-methylpyridin-3-ol (1.03 g, 5.0 mmol) was suspended in DMF (50 mL) and methyl iodide (0.31 mL, 5 mmol) was added at rt. The reaction mixture was stirred over a period of 19 h and a further portion of methyl iodide (0.125 mL, 2 mmol) was added and stirred over a period of 23 h. Aq. K₂CO₃ solution (10 mL) and water (50 mL) was added and extracted with ethyl acetate (2×50 mL). Combined organic layers were dried over MgSO₄ (10 g) and evaporated to a volume of 20 mL. After 3 days at room temperature, the crystallized product was filtered off and dried to give (600 mg) the title compound as a light beige solid.

Example 8

Redox Metal Ion Binding Affinity (Cu and Fe)

The AGE inhibition by these types of compounds is believed to occur when the compounds interfere with the role of the required redox metal ions in the oxidative breakdown of the Amadori intermediates to advanced glycation end products ("glycoxidation"). We have measured the affinity of the compounds for cupric, ferrous and ferric ions in several cases by following visible spectroscopic changes. These spectral titrations usually involve adding varying amounts of compound to a fixed amount of metal ion in a suitable buffer having low metal ion affinity under physiological pH conditions. In cases of extreme affinity, binding constants were estimated in a competitive assay mode. Table 1 provides some data that has been obtained in this way.

It will be noted that BST-605 is superior to BST-4997 in this regard, and the latter compound was superior to pyridoxamine. The N-methylpiperazine side-chain of BST-4997 thus unexpectedly enhanced the metal ion binding affinity, which could not have been predicted a priori.

Binding affinity is measured as the dissociation constants $K_d$ (units of concentration). All measurements were done by visible spectroscopy by monitoring the spectrum of the complex formed by each compound near its wavelength maximum, which depends on the metal ion being studied. All Fe wavelengths were 480 nm except for 430 nm for pyridoxamine.

TABLE 1

| Compound | $Cu^{2+} K_d$ (μM) | $Fe^{2+} K_d$ (mM) | $Fe^{3+} K_d$ (mM) |
|---|---|---|---|
| Pyridoxamine | 39 +/− 15 | 49 +/− 9 | 59 +/− 13 |
| BST-4997 | 1.13 +/− 0.09 | 0.69 +/− 0.13 | 0.61 +/− 0.09 |
| BST-605 | 0.13 +/− 0.04 | 0.72 +/− 0.14 | 0.52 +/− 0.04 |
| C-14547 | 7.01 +/− 1.69 | | |
| BST-4996 | | | 0.59 +/− 0.11 |

Example 9

AGE Inhibition Efficacy In Vitro

Using a novel modification of the AGE Inhibition assay, we have determined the post-Amadori AGE inhibition potency for compounds of interest. The experiments were designed to determine the half-maximal inhibitory concentration of compounds ("IC50 values") for inhibiting the conversion of Amadori intermediates to advanced glycation end products. The post Amadori AGE/CML ELISA assay has been developed to a 384 well format for rapidly testing potential inhibitors prepared from DMSO stocks. Assay signal to background ratios are high, at greater than 20:1. Results in this format for AGE inhibitors agree well with previous data, providing some measure of method validation, making the assay is robust and reliable. Compounds for testing were dissolved at 100 mM or their maximum concentration in 100% DMSO. 100 mM is the DMSO stock concentration necessary to detect potential inhibitors that have an effective concentration similar to that of pyridoxamine. A subset of compounds were not fully soluble in DMSO at concentrations as low as 10 mM. Due to low aqueous solubility, an initial screening of compounds was usually carried out in dilute form across a 100 fold concentration range. Tested concentrations were from 0.2-20 μM to 2-200 μM, with the compound concentration tested being dependent upon the original solubility in DMSO. When necessary, the activity of compounds was subsequently confirmed in a more thorough repeat test against AGE formation from both RNase Amadori and BSA Amadori. Typically, from DMSO stocks, two stock plates were made. Each well contained 50 μL.

The stock plate #2 was then frozen at −20° C. during preparation. Later, stock plate #2 was removed from the freezer and allowed to thaw for 30 minutes. The compounds in the plate were then mixed repeatedly with a pipettor and diluted 5× into 0.01 N HCl in $H_2O$.

Further dilutions were then carried out spanning two orders of magnitude of concentration. After the compounds were diluted, 10 ul of phosphate buffer was added to each well and mixed to neutralize the solution before protein addition. Next 15 μL of 0.333 mg/mL of RNase-Amadori in phosphate buffer was added from a stock of ribose-RNAse prepared at 10.7 mg/mL. These constitute the AGE reaction mixtures. All AGE reactions proceeded for 20 hours at 37° C. Reactions were then diluted 50 fold into coating buffer by 10× then 5× serial dilution. Coating proceeded at 37° C. for two hours. Final protein was 0.1 μg/well in 384 well plates (2 μg/mL). ELISA was carried out similarly to before using the primary antibody BST-3CK at 1:10000 dilution, and the secondary antibody labeled with DELPHIA Europium GAR at 1:4000 dilution.

Pyridoxamine served as a reference to highlight the potency of BST-4997. In the present instance, the latter compound now serves as reference to highlight the unanticipated greater potency of BST-605. Comparative data are given in Table 2 below. The unexpected 6-fold potency of BST-605 over BST-4997 (and 50-fold over pyridoxamine) contrasts with the observation that the 5'-amino derivative C-14547 as well as the 5'-acetamido derivative C-14521 had significantly weaker activity than BST-4997. Thus introducing the nitrogen at the 5'-position in itself does not account for the enhanced activity. The heterocyclic piperazine ring thus provides the key to the enhancement, and we anticipate other similar rings would be advantageous.

TABLE 2

| Compound | $IC_{50}$ | Potency Relative to BST-4997 |
|---|---|---|
| Pyridoxamine | 5 mM | 0.12 |
| BST-4997 | 0.6 mM | (1) |
| C-14521 | 2-3 mM | 0.2-0.3 |
| C-14547 | 1-2 mM | 0.3-0.6 |
| BST-605 | 0.1 mM | 6 |

Example 10

Cell Based Toxicity Assay

Hepatotoxicity is one of the major causes of drug failure in the clinic. HepG2 cells are human cells derived from a liver tumor, and express many of the proteins and detoxification pathways of normal hepatocytes, and so make a reasonable model for initial cellular toxicity testing of candidate compounds. The test is based on the active conversion of 3-[4,5-dimethylthiazol-2-yl]-2,5-dephenyltetrazolium bromide (MTT) by mitochondrial oxidation-reduction reactions into blue formazan crystals. Decreased crystal formation corresponds to decreased cell viability. Azide and chlorpromazine served as a positive controls
Need:
10×MTT stock solution (5 mg/ml MTT in 0.9% NaCl)
0.04 N HCl in isopropanol
Compound stocks: 100 mM in 100% DMSO
MTT working solution: diluting 10×MTT stock into culture medium.
Test article in cell culture medium; Final DMSO concentration on the cells varies with the compound concentration (Final concentration of solvents such as DMSO should be kept at or below 1%)
Method:
1. Aspirate culture medium from HepG2 cells. Replace culture medium with test article dissolved in culture medium.
2. Incubate in 37° C., 5% $CO_2$ incubator for 16-24 hours.
3. Aspirate the medium from the cells; replace with an equal volume of 37° C. MTT working solution.
4. Incubate for 3 hours.
5. Replace MTT solution with an equal volume of acidified isopropanol.
6. Place solution in the refrigerator for 12-24 hours.
7. Place solution on an orbital shaker to dissolve any fomazan precipitate.
8. Read the absorbance of the solution at 570 nm.

Figure 3:
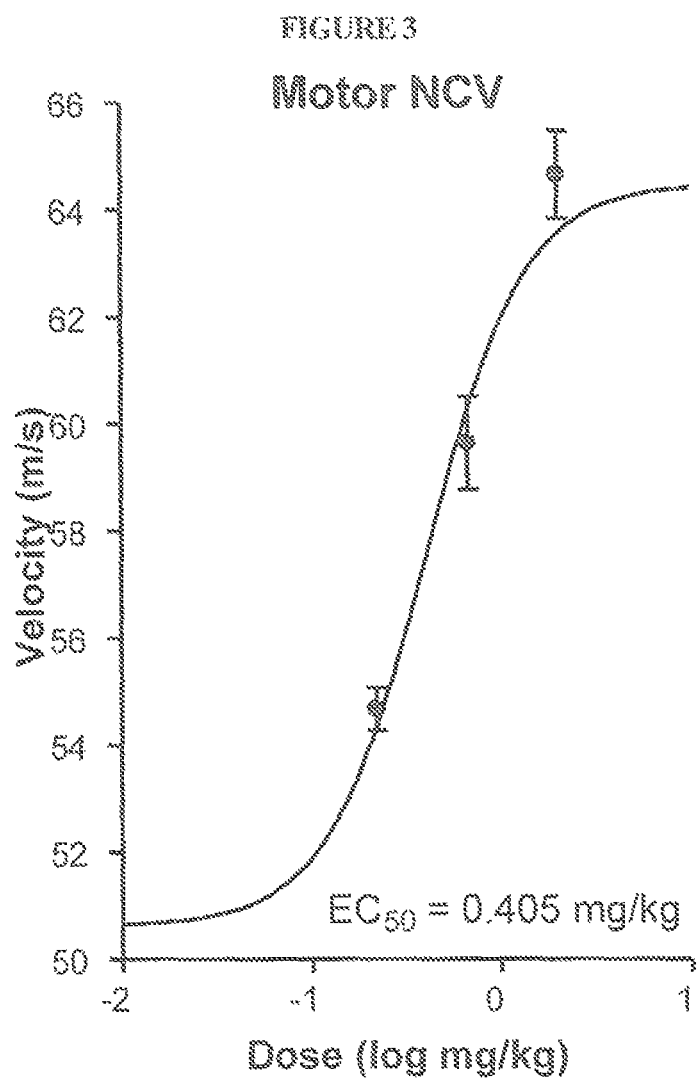
FIG. 3 is a graphical representation of the effect of BST-605 on the restoration of nerve conduction velocity in motor (sciatic nerve) neurons in streptozotocin diabetic rats.

Several of the compounds of interest were tested at several concentrations for potential acute toxicity in the HepG2 cell-based assay system. FIGS. 2 and 3 summarize the results of the assay; in all these graphs, cell viability increases with bar height.

FIG. 2 provides comparative data for pyridoxamine (PM), BST-4997 (also, the free base of this compound which is referred to as BST-998), a 5'-acetyl ester of BST-4997 (BST-146) which is rapidly hydrolyzed to the parent, and BST-605.

At a fixed concentration (1 mM), it was observed that BST-605 shows no acute toxicity in this assay, whereas BST-4997 shows some evidence of toxicity.

Example 11

Maximum Tolerated Dose (MTD) Safety Study in Mice

A seven day repeat oral gavage study was carried out in male mice in order to detect any obvious signs of clinical toxicity upon administration of BST-605. For comparison, two groups were dosed with BST-4997 and BST-146 (acetyl ester of BST-4997 that is rapidly hydrolyzed to parent BST-4997). Dosing was done daily at 10, 30 and 100 mg/kg/day, and blood draws were taken at the end of study at 1, 2, 4 and 8 h post-dosing.

The results confirmed that BST-4997 dosed animals suffered significant toxicity at and above 30 mg/kg/day, leading to significant loss of the animals. In contrast, no adverse clinical signs or gross examination findings were noted for any mice in the BST-605 dose groups. BST-605 thus possesses marked superiority over BST-4997 with regard to in vivo toxicity and represents a significant advance.

Example 12

In Vivo Plasma Concentration and Metabolites

The plasma drawn from the mice in the above MTD study was examined by an HPLC fluorescence method for the presence of parent drug at different times as well as for the possible presence of metabolites. A similar examination was done for plasma samples from the fewer surviving mice that received BST-4997. An HPLC fluorescence method was developed to assay for parent drugs and possible metabolites of each drug. The HPLC method was further adapted for LC-MS/MS study by changing from phosphoric acid to volatile 20 mM ammonium acetate. Parent drugs were detected and quantified, and the plasma concentration that was proportional to dose for BST-605 though not for BST-4997. This indicates improved pharmacokinetic behavior for BST-605.

Novel metabolites were detected and quantified for BST-605 and BST-4997, and their retention times and "concentrations" (assuming similar fluorescence to parents) were measured. Analysis of such metabolites indicated that the parent compound had been oxidized and/or undergone glucuronidation. Possible structures for the metabolites include the following:

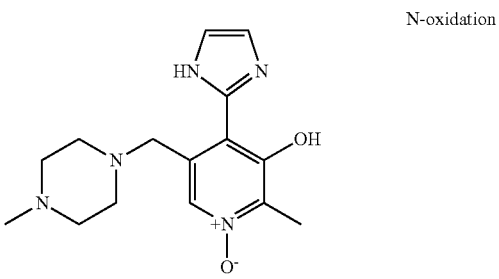

N-oxidation

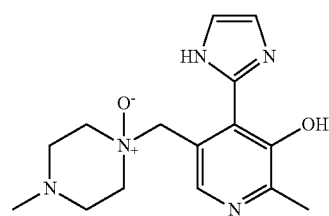

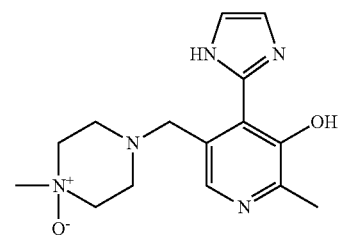

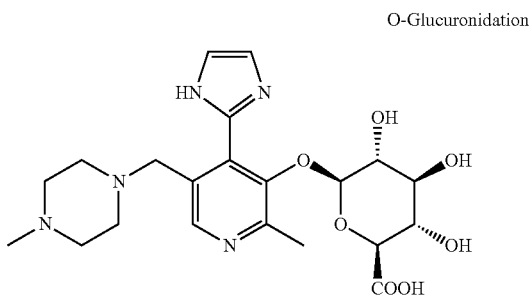

O-Glucuronidation

Example 13

Efficacy Study in STZ Rat Model of Diabetic Neuropathy

In vivo, BST-605 ameliorates diabetic complications in a STZ rat model in proportion to its potency in the post-Amadori AGE inhibition assay. The STZ rat model has been described previously in WO 2004/019889. Our aim was to ascertain whether BST-605 treatment could correct nerve dysfunction in streptozotocin (STZ)-diabetic rats. Animals were made diabetic for 6 weeks, following which they were treated (n=6) for 2 weeks with BST-605 given in the drinking water at concentrations adjusted to correspond to doses of 0.22, 0.67 and 2.0 mg/kg/day. They were compared to control non-diabetic rats (n=10).

FIG. 3 provides the dose-response curve for restoration of nerve conduction velocity in motor (sciatic nerve) neurons, demonstrating efficacy at very low concentrations. Motor NCV was tested between the sciatic notch and knee for the nerve branch to tibialis anterior muscle, as described in Cameron et al., Q. J. Exp. Physiol. 74:917-926 (1989); and Cameron et al, Exp. Neurol. 92:757-761 (1986).

Figure 4:
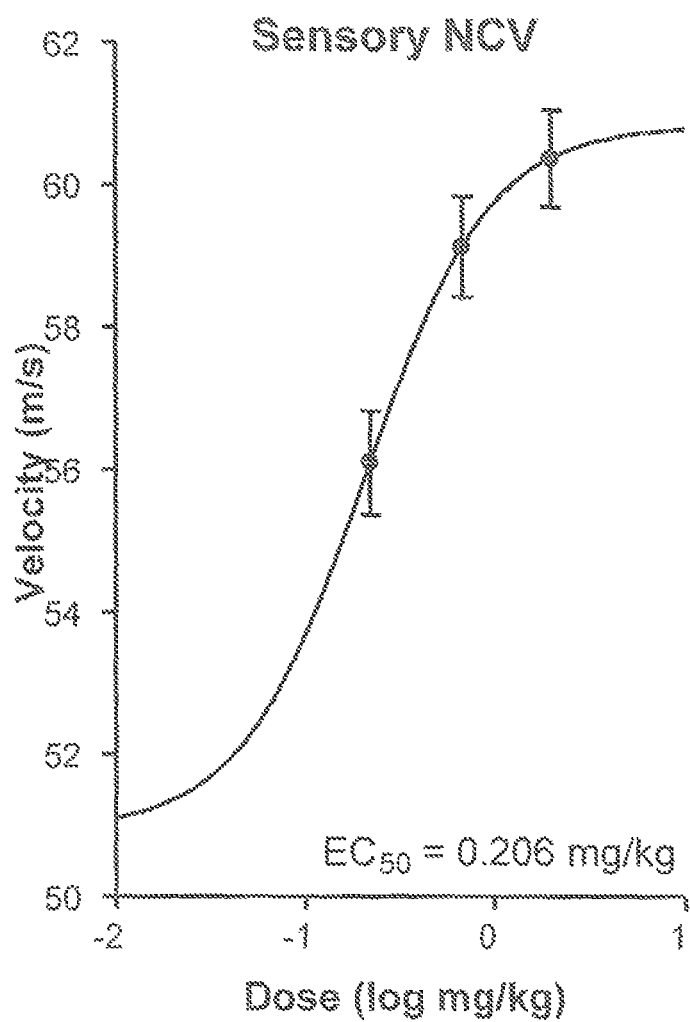
FIG. 4 is a graphical representation of the effect of BST-605 on the restoration of nerve conduction velocity in sensory (saphenous) neurons in streptozotocin diabetic rats.

FIG. 4 provides the dose-response curve for restoration of nerve conduction velocity in sensory (saphenous) neurons, demonstrating efficacy at very low concentrations. Saphenous sensory NCV was measured between the groin and ankle.

FIG. 5 compares BST-605 to BST-4997 and pyridoxamine showing the progression in increased potency that follows the progression in post-Amadori AGE inhibition.

We have further established a causal the link between administration of such post-Amadori AGE inhibitors and therapeutic benefit by observing that BST-4997 treated STZ rats demonstrated an actual decrease in AGE levels in the nerve vasculature. This was done by quantitative measurements of tissue staining for carboxymethyllysine (CML) AGEs, using anti-CML antibodies. A significant decrease in AGE staining was observed for animals treated with BST-4997 as compared to diabetic controls.

A determination of drug exposure was also made from plasma collected from STZ rats at sacrifice that were dosed at the lowest two doses. Drug exposure was observed and measured for BST-605, and its major metabolites were detected. The detection of parent drugs and metabolites in the STZ rat, as in the mice plasma, confirms that sufficient exposure to the drug occurred in the studies so as to make the toxicity findings and in vivo efficacy reflective of drug administration.

It is understood that the foregoing detailed description and accompanying Examples are merely illustrative and are not to be taken as limitations upon the scope of the invention, which is defined by the appended claims. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

We claim:

1. A compound of the formula, or a pharmaceutically acceptable salt thereof, wherein
X is N or N—O;
G is —H;
A is of the formula, wherein
Y is N or N-oxide; and
ring C is:
(i) monocyclic;
(ii) saturated; and
(iii) contains 1 or 2 total heteroatoms, and 5 or 6 total atoms, wherein
the remaining heteroatom moiety is O, S, or $NR^{N1}$, and the carbon atoms are each optionally substituted with one or two $R^C$ wherein
$R^{N1}$ is —H, -oxide, —$(C_1$-$C_6)$alkyl, —$(C_2$-$C_6)$alkenyl, —$(C_1$-$C_6)$alkynyl, —$(C_1$-$C_6)$haloalkyl, or —$(C_1$-$C_6)$alkanoyl;
each $R^C$ is independently —$Z^1$-M-$Z^2$—$R^Z$, wherein $Z^1$, M and $Z^2$ are absent, and
$R^Z$ is —H, —$(C_1$-$C_6)$alkyl, —$(C_2$-$C_6)$alkenyl, —$(C_1$-$C_6)$alkynyl, or —$(C_1$-$C_6)$haloalkyl, —$(C_3$-$C_8)$cycloalkyl, —$(C_1$-$C_6)$alkylaryl, -heterocycle, -aryl, or -heteroaryl;
B is imidazolyl wherein each carbon atom is substituted by $R^3$, wherein
each $R^3$ is independently $R^{Z3}$, wherein
$R^{Z3}$ is —H, —$(C_1$-$C_6)$alkyl, —$(C_1$-$C_6)$haloalkyl, —$(C_3$-$C_8)$cycloalkyl, —$(C_1$-$C_6)$alkylaryl, -heterocycle, -aryl, or -heteroaryl; and
$R^2$, and $R^6$ are independently —H, -halogen, —$NO_2$, —CN, or $R^{Z6}$ wherein $R^{Z6}$ is —$(C_1$-$C_6)$alkyl or —$(C_1$-$C_6)$haloalkyl.

2. The compound according to claim 1, wherein
ring C contains 2 heteroatoms, and 5 total atoms, wherein
the remaining heteroatom moiety is O, S, or $NR^{N1}$, and
the carbon atoms are each optionally substituted with one or two $R^C$.

3. The compound according to claim 1, wherein
ring C contains 2 heteroatoms, and 6 total atoms, wherein the remaining heteroatom moiety is O, S, or $NR^{N1}$, and the carbon atoms are each optionally substituted with one or two $R^C$.

4. The compound according to claim 1, wherein $R^{Z3}$ is —H, —$(C_1$-$C_6)$alkyl or —$(C_1$-$C_6)$haloalkyl.

5. The compound according to claim 1, wherein $R^2$ and $R^6$ are each independently —H, -halogen, —$NO_2$, —CN, —$(C_1$-$C_6)$alkyl or —$(C_1$-$C_6)$haloalkyl.

6. The compound according to claim 1, wherein $R^{N'}$ is —H, —$(C_1$-$C_6)$alkyl or —$(C_1$-$C_6)$haloalkyl.

7. The compound according to claim 1, wherein ring C contains 2 heteroatoms, and 5 total atoms, wherein the remaining heteroatom moiety is O or $NR^{N1}$, and the carbon atoms are each optionally substituted with one or two $R^C$.

8. The compound according to claim 1, wherein ring C contains 2 heteroatoms, and 6 total atoms, wherein the remaining heteroatom moiety is O or $NR^{N1}$, and the carbon atoms are each optionally substituted with one or two $R^C$.

9. The compound according to claim 8, wherein $R^{Z3}$ is —H, —$(C_1$-$C_6)$alkyl or —$(C_1$-$C_6)$haloalkyl.

10. The compound according to claim 8, wherein $R^2$ and $R^6$ are each independently —H, -halogen, —$NO_2$, —CN, —$(C_1$-$C_6)$alkyl or —$(C_1$-$C_6)$haloalkyl.

11. The compound according to claim 8, wherein $R^{N'}$ is —H, —$(C_1$-$C_6)$alkyl or —$(C_1$-$C_6)$haloalkyl.

12. The compound according to claim 8, wherein ring C contains 2 heteroatoms, and 5 total atoms, wherein the remaining heteroatom moiety is $NR^{N1}$, and the carbon atoms are each optionally substituted with one or two $R^C$.

13. The compound according to claim 8, wherein ring C contains 2 heteroatoms, and 6 total atoms, wherein the remaining heteroatom moiety is $NR^{N1}$, and the carbon atoms are each optionally substituted with one or two $R^C$.

14. The compound according to claim 13, wherein $R^{Z3}$ is —H, —$(C_1$-$C_6)$alkyl or —$(C_1$-$C_6)$haloalkyl.

15. The compound according to claim 13, wherein $R^2$ and $R^6$ are each independently —H, -halogen, —$NO_2$, —CN, —$(C_1$-$C_6)$alkyl or —$(C_1$-$C_6)$haloalkyl.

16. The compound according to claim 13, wherein $R^{N'}$ is —H, —$(C_1$-$C_6)$alkyl or —$(C_1$-$C_6)$haloalkyl.

17. The compound according to claim 1, wherein ring C contains 2 heteroatoms, and 5 total atoms, wherein the remaining heteroatom moiety is $NR^{N1}$, and the carbon atoms are unsubstituted;
$R^{Z3}$ is —H, —$(C_1$-$C_6)$alkyl or —$(C_1$-$C_6)$haloalkyl;
$R^2$ and $R^6$ are each independently —H, -halogen, —$NO_2$, —CN, —$(C_1$-$C_6)$alkyl or —$(C_1$-$C_6)$haloalkyl; and
$R^{N'}$ is —H, —$(C_1$-$C_6)$alkyl or —$(C_1$-$C_6)$haloalkyl.

18. The compound according to claim 1, wherein ring C contains 2 heteroatoms, and 6 total atoms, wherein the remaining heteroatom moiety is O, S, or $NR^{N1}$, and the carbon atoms are unsubstituted;
$R^{Z3}$ is —H, —$(C_1$-$C_6)$alkyl or —$(C_1$-$C_6)$haloalkyl;
$R^2$ and $R^6$ are each independently —H, -halogen, —$NO_2$, —CN, —$(C_1$-$C_6)$alkyl or —$(C_1$-$C_6)$haloalkyl; and
$R^{N'}$ is —H, —$(C_1$-$C_6)$alkyl or —$(C_1$-$C_6)$haloalkyl.

19. The compound according to claim 1 that is:
4-(1H-imidazol-2-yl)-2-methyl-5-((4-methylpiperazin-1-yl)methyl)pyridin-3-ol
or a pharmaceutically acceptable salt thereof.

20. A pharmaceutical composition comprising the compound of claim 1 and a pharmaceutically acceptable carrier.

* * * * *